US010555879B2

(12) United States Patent
Lei et al.

(10) Patent No.: US 10,555,879 B2
(45) Date of Patent: *Feb. 11, 2020

(54) POLYUREA CAPSULE COMPOSITIONS

(71) Applicant: International Flavors & Fragrances Inc., New York, NY (US)

(72) Inventors: Yabin Lei, Holmdel, NJ (US); Lewis Michael Popplewell, Morganville, NJ (US); Li Xu, Edison, NJ (US); John Brahms, Morris Plains, NJ (US); Xiang Fei, Buffalo Grove, IL (US)

(73) Assignee: INTERNATIONAL FLAVORS & FRAGRANCES INC., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/045,179

(22) Filed: Jul. 25, 2018

(65) Prior Publication Data
US 2018/0353399 A1 Dec. 13, 2018

Related U.S. Application Data

(63) Continuation of application No. 15/047,364, filed on Feb. 18, 2016, now Pat. No. 10,085,925, which is a continuation-in-part of application No. 14/911,433, filed as application No. PCT/US2014/051309 on Aug. 15, 2014, now Pat. No. 10,092,486, which is a continuation-in-part of application No. 13/968,862, filed on Aug. 16, 2013, and a continuation-in-part of application No. 13/969,038, filed on Aug. 16, 2013, now Pat. No. 9,687,424, and a continuation-in-part of application No. 13/967,800, filed on Aug. 15, 2013.

(60) Provisional application No. 62/272,740, filed on Dec. 30, 2015.

(51) Int. Cl.
| | |
|---|---|
| *A61K 8/11* | (2006.01) |
| *A61K 8/73* | (2006.01) |
| *A61K 8/81* | (2006.01) |
| *A61K 8/84* | (2006.01) |
| *A61K 8/87* | (2006.01) |
| *A61K 8/92* | (2006.01) |
| *A61Q 19/00* | (2006.01) |
| *C11D 17/00* | (2006.01) |
| *C11D 3/50* | (2006.01) |
| *A61Q 3/00* | (2006.01) |
| *A61Q 5/12* | (2006.01) |
| *A61Q 13/00* | (2006.01) |

(52) U.S. Cl.
CPC .............. *A61K 8/11* (2013.01); *A61K 8/731* (2013.01); *A61K 8/8111* (2013.01); *A61K 8/8117* (2013.01); *A61K 8/84* (2013.01); *A61K 8/87* (2013.01); *A61K 8/922* (2013.01); *A61Q 19/00* (2013.01); *C11D 3/505* (2013.01); *C11D 17/0039* (2013.01); *A61K 2800/10* (2013.01); *A61K 2800/412* (2013.01); *A61Q 5/12* (2013.01); *A61Q 13/00* (2013.01)

(58) Field of Classification Search
CPC ........ A61K 8/922; A61K 8/87; A61K 8/8111; A61K 8/731; A61K 8/11; A61K 8/84; A61K 8/8117; A61K 2800/412; A61K 2800/10; C11D 3/505; C11D 17/0039; A61Q 19/00; A61Q 13/00; A61Q 5/12
See application file for complete search history.

(56) References Cited

U.S. PATENT DOCUMENTS

| | | |
|---|---|---|
| 3,743,601 A | 7/1973 | Rao |
| 3,963,680 A | 6/1976 | O'Keefe |
| 4,021,595 A | 5/1977 | Kiritani |
| 4,280,833 A | 7/1981 | Beestman |
| 4,309,213 A | 1/1982 | Graber |
| 4,428,983 A | 1/1984 | Nehen |
| 4,563,212 A | 1/1986 | Becher |
| 4,608,227 A | 8/1986 | Greiner |
| 4,640,709 A | 2/1987 | Beestman |
| 4,785,048 A | 11/1988 | Chao |
| 4,798,862 A | 1/1989 | Gillis |
| 5,164,126 A | 11/1992 | Kalishek |
| 5,304,448 A | 4/1994 | Keoshkerian |
| 5,324,584 A | 6/1994 | Juang |
| 5,635,211 A | 6/1997 | Nehen |
| 5,705,174 A | 1/1998 | Benoff |
| 5,866,153 A | 2/1999 | Hasslin |
| 5,925,595 A | 7/1999 | Seitz |

(Continued)

FOREIGN PATENT DOCUMENTS

| | | |
|---|---|---|
| EP | 1693104 A1 | 8/2006 |
| JP | 5068970 A | 6/1975 |

(Continued)

OTHER PUBLICATIONS

Carvalho et al. Food Research International, 61 (2014), pp. 236-245. (Year: 2014).*

(Continued)

*Primary Examiner* — Doan T Phan
(74) *Attorney, Agent, or Firm* — Licata & Tyrrell P.C.

(57) ABSTRACT

A microcapsule composition useful in delivering an active material contains a first microcapsule and a second microcapsule. The first microcapsule has a zeta potential of 10 mV or greater, the second microcapsule has a zeta potential of 5 mV or less, and the weight ratio of the first microcapsule and the second microcapsule is between 1:10 and 10:1. Also disclosed are consumer products containing such a microcapsule composition.

20 Claims, No Drawings

(56) References Cited

U.S. PATENT DOCUMENTS

| | | | |
|---|---|---|---|
| 6,133,197 | A | 10/2000 | Chen |
| 6,340,653 | B1 | 1/2002 | Scher |
| 6,586,107 | B2 | 7/2003 | Klug |
| 6,797,670 | B2 | 9/2004 | Kleban |
| 6,964,994 | B1 | 11/2005 | Antonietti |
| 7,125,835 | B2 | 10/2006 | Bennett |
| 7,632,789 | B2 | 12/2009 | Brain |
| 8,026,206 | B2 | 9/2011 | Sajic |
| 8,299,011 | B2 | 10/2012 | Lei |
| 2002/0079599 | A1 | 6/2002 | Kleban |
| 2004/0121155 | A1 | 6/2004 | Matsunami |
| 2004/0156742 | A1 | 8/2004 | Milan |
| 2004/0254066 | A1 | 12/2004 | Ramarao |
| 2005/0153135 | A1 | 7/2005 | Popplewell |
| 2005/0153839 | A1 | 7/2005 | Tamura |
| 2005/0161843 | A1 | 7/2005 | Wang |
| 2005/0271735 | A1 | 12/2005 | Stover |
| 2007/0042182 | A1 | 2/2007 | Markus |
| 2007/0138672 | A1 | 6/2007 | Lee |
| 2007/0202063 | A1 | 8/2007 | Dihora |
| 2008/0103265 | A1 | 5/2008 | Schocker |
| 2008/0131695 | A1 | 6/2008 | Aouad |
| 2008/0187596 | A1 | 8/2008 | Dihora |
| 2008/0200363 | A1 | 8/2008 | Smets |
| 2008/0206291 | A1 | 8/2008 | Ouali |
| 2009/0053161 | A1 | 2/2009 | Nguyen |
| 2009/0259300 | A1 | 10/2009 | Dorogy |
| 2009/0274905 | A1* | 11/2009 | Schwantes ............... A61K 8/11 428/402 |
| 2010/0009893 | A1 | 1/2010 | Cavin |
| 2010/0086575 | A1 | 4/2010 | Dihora |
| 2010/0119679 | A1 | 5/2010 | Dihora |
| 2011/0077188 | A1 | 3/2011 | Ouali |
| 2011/0077375 | A1 | 3/2011 | Kulke |
| 2011/0230390 | A1 | 9/2011 | Ouali |
| 2011/0245141 | A1 | 10/2011 | Gizaw |
| 2012/0016139 | A1 | 1/2012 | Screen |
| 2012/0148644 | A1 | 6/2012 | Popplewell |
| 2012/0276210 | A1* | 11/2012 | Dihora .................... A61K 8/11 424/497 |
| 2013/0109569 | A1 | 5/2013 | Dave |
| 2013/0330292 | A1 | 12/2013 | Lei |
| 2013/0337023 | A1 | 12/2013 | Lei |
| 2014/0017287 | A1 | 1/2014 | Lei |
| 2014/0193350 | A1* | 7/2014 | Bauer .................... A61K 8/347 424/70.11 |

FOREIGN PATENT DOCUMENTS

| | | |
|---|---|---|
| WO | 2004098767 A1 | 11/2004 |
| WO | 2006006003 A1 | 1/2006 |
| WO | 2007137441 A1 | 12/2007 |
| WO | 2008031241 A1 | 3/2008 |
| WO | 2009091726 A1 | 7/2009 |
| WO | 2009103615 A1 | 8/2009 |
| WO | 2011104893 A1 | 9/2011 |
| WO | 2011154893 A1 | 12/2011 |
| WO | 2011161265 A2 | 12/2011 |
| WO | 2012107323 A1 | 8/2012 |
| WO | 2013000587 A1 | 1/2013 |
| WO | 2013059167 A2 | 4/2013 |
| WO | 2013092958 A1 | 6/2013 |

OTHER PUBLICATIONS

BASF (2010). "Lupasol®types". Retrieved on Jun. 14, 2017. Retrieved from the Internet <URL:http://www.carytrad.com.tw/chemical/download/basf/08_080613oeLupasol%20types.pdf>, pp. 1-10.

Chinese First Office Action dated Jan. 30, 2014 for Application No. CN 201010548980.0.

Dow Plastics—"PAPI135". Retrieved on Jan. 3, 2017. Retrieved from the internet <URL:http://msdssearch.dow.com/PublishedliteratureDOWCOM/dh_003f/0901b8038003f163.pdf>.

EP Extended Search Report dated Mar. 31, 2017 from 14836347.9 filed Aug. 15, 2014.

International Preliminary Report on Patentability in PCT/US2014/051309 dated Feb. 16, 2016.

International Search Report and Written Opinion in PCT/US2014/051309 dated Nov. 4, 2014.

Office Communication dated Oct. 18, 2011 from U.S. Appl. No. 12/562,578, filed Sep. 18, 2009.

Office Communication dated Aug. 21, 2012 from U.S. Appl. No. 13/163,320, filed Jun. 17, 2011.

Office Communication dated Nov. 21, 2012 from U.S. Appl. No. 13/163,320, filed Jun. 17, 2011.

Office Communication dated Jan. 4, 2017 from U.S. Appl. No. 15/047,364, filed Feb. 18, 2016.

Office Communication dated Jan. 5, 2017 from U.S. Appl. No. 14/911,433, filed Feb. 10, 2016.

Office Communication dated Jun. 30, 2017 from U.S. Appl. No. 15/047,590, filed Feb. 18, 2016.

* cited by examiner

POLYUREA CAPSULE COMPOSITIONS

CROSS-REFERENCE TO RELATED APPLICATIONS

This application is a continuation of U.S. application Ser. No. 15/047,364, filed on Feb. 18, 2016. U.S. application Ser. No. 15/047,364 claims benefit of priority to U.S. Provisional Ser. No. 62/272,740 filed Dec. 30, 2015 and is a continuation-in-part of to U.S. application Ser. No. 14/911,433 filed Feb. 10, 2016. U.S. application Ser. No. 14/911,433 is a national phase entry under 35 USC 371 for International Application No. PCT/US14/51309 filed on Aug. 15, 2014. International Application No. PCT/US14/51309 is a continuation-in-part of three US patent applications: U.S. application Ser. No. 13/967,800 filed Aug. 15, 2013; U.S. application Ser. No. 13/968,862 filed Aug. 16, 2013; and Ser. No. 13/969,038 filed on Aug. 16, 2013, now issued as U.S. Pat. No. 9,687,424. The contents of the above-mentioned applications are incorporated herein by reference in their entirety.

BACKGROUND

Nano- or micro-encapsulation is used in a variety of different applications where there is a need to deliver, apply, or release an active material including a fragrance, flavor, and malodor counteraction agent to a target area in a time-delayed or controlled manner. Various techniques for preparing capsules are known in the art and are used, depending on the contents to be encapsulated, the environment in which the capsules should retain their integrity and the desired release mechanism.

Interfacial polycondensation is a known technique for preparing capsules and versatile capsule wall materials are used including polyureas and polyurethanes (WO 2011/154893, WO 2012/107323, US 2011/0077188, U.S. Pat. Nos. 5,635,211, 6,586,107, and 6,797,670). Such wall materials are produced by having a first phase which is water-immiscible and includes a polyfunctional isocyanate, i.e., a polyisocyanate having two or more isocyanate groups, and a second aqueous phase which includes (i) a polyfunctional alcohol (i.e., a polyol) having two or more —OH groups for obtaining a polyurethane capsule wall, or (ii) a polyfunctional amine (i.e., a polyamine) having two or more —$NH_2$ and/or —NH groups for obtaining a polyurea capsule wall.

If the active material to be encapsulated is hydrophobic, it will be included in the water-immiscible phase, thereafter the two phases are mixed by high shear mixing to form an oil-in-water emulsion. In this emulsion, the polycondensation reaction will take place. Thus, the small droplets of the water-immiscible phase will be surrounded by the capsule wall formed by polycondensation of the isocyanate and the polyalcohol or polyamine as starting materials. Conversely, if the material to be encapsulated is hydrophilic, it will be included in the aqueous phase and the mixture of the two phases converted into a water-in-oil emulsion. The polycondensation reaction will then form capsule walls surrounding the droplets of water-miscible phase. Suitable emulsifiers are often utilized to aid in the preparation and stabilization of the emulsion.

Suitable raw materials and processes for preparing capsules by polycondensation are described in U.S. Pat. No. 4,640,709 and the literature described therein. As is exemplified therein, and also in U.S. Pat. No. 6,133,197, polyurea and polyurethane capsules are often used for rugged applications, such as for encapsulation of agrochemicals, e.g., herbicides and pesticides, where slow time-release is desired to set the agents free. For such applications, the capsules also require a relatively high mechanical strength. For the polycondensation reaction, suitable diisocyanate and symmetrical triisocyanate starting materials are disclosed in the prior art.

WO 2011/154893 discloses a process for the preparation of capsules, which includes mixing at least one aliphatic polyisocyanate and of at least one aromatic polyisocyanate, wherein the molar ratio between the two polyisocyanates is between 75:25 and 20:80.

WO 2013/000587 discloses a process for the preparation of polyurea capsules, which includes dissolving at least one polyisocyanate having at least two isocyanate functional groups, in a perfume to form a solution; adding to the solution an aqueous solution of an emulsifier or of a colloidal stabilizer; and adding to the mixture to 3,5-diamino-1,2,4-triazole to form a polyurea wall.

U.S. Pat. No. 5,304,448 describes an encapsulated toner composition using reaction of amino acids and polyisocyanates.

Known polyurea or polyurethane capsules face various issues, e.g., low olfactory intensity, low stability, and high toxicity. Their deposition to target surfaces is also problematic.

There is a need to develop a safe, stable, and high efficient capsules for use in laundry, washing, cleaning, surface care and personal and skin care. For such applications quicker and easier release and/or less mechanical strength are often desirable. Also, it would be desirable to more precisely influence the capsule wall permeability and other capsule wall properties to achieve the desired release profile and consumer benefits.

SUMMARY OF THE INVENTION

This invention is based on the discovery that certain capsule compositions possess unexpected desirable properties including high perceived olfactory intensity, prolonged stability, low toxicity, and improved deposition.

Accordingly, one aspect of this invention relates to a microcapsule compositions comprising a first microcapsule and a second microcapsule, in which the first microcapsule has a zeta potential of 10 mV or greater (e.g., 25 mV or greater, 40 mV or greater, 40 to 200 mV, and 40 to 100 mV), the second microcapsule has a zeta potential of 5 mV or less (e.g., −5 to 5 mV, −10 mV or less, −20 mV or less, −40 mV or less, −20 to −200 mV, and −20 to −100 mV), and the weight ratio of the first microcapsule and the second microcapsule is between 1:10 and 10:1 (e.g., 20:80 to 80:20, 30:70 to 70:30, and 40:60 to 60:40).

The first microcapsule contains a first oil core and a first microcapsule wall encapsulating the first oil core.

The first microcapsule wall is typically formed of a first encapsulating polymer that is the reaction product of a multi-functional nucleophile and a multi-functional electrophile. Suitable multi-functional nucleophiles include a branched polyethyleneimine, a mixture of the branched polyethyleneimine and a polyfunctional amine, and a mixture of the branched polyethyleneimine and a polyfunctional alcohol. Exemplary polyfunctional amines include, but are not limited to hexamethylenediamine, ethylenediamine, 1,3-diaminopropane, 1,4-diamino-butane, diethylenetriamine, pentaethylenehexamine, bis(3-aminopropyl)amine, bis(hexanethylene)triamine, tris(2-aminoethyl)amine, triethylene-tetramine, N,N'-bis(3-aminopropyl)-1,3-propanediamine, tetraethylenepentamine, penta-ethylenehexamine, chitosan, nisin, gelatin, 1,3-diamino-guanidine, 1,1-dimethylbiguanide, guanidine, arginine, lysine, ornithine, and combinations thereof. The multi-functional electrophile has a first functional group and a second functional group, each of which, independently, is an electrophilic group reactive towards the multi-functional nucleophile.

Preferably, the first encapsulating polymer is the reaction product of a branched polyethyleneimine and a polyisocyanate. The branched polyethyleneimine can have a molecular weight of 750 to 50000 Dalton ("Da"). Exemplary polyisocyanates are polymeric methylene diphenyl diisocyanates, hydrogenated polymeric methylene diphenyl diisocyanates, methylene diphenyl diisocyanates, hydrogenated methylene diphenyl diisocyanates, trimers of hexamethylene diisocyanate, trimers of isophorone diisocyanate, biurets of hexamethylene diisocyanate, polyisocyanurates of toluene diisocyanate, trimethylol propane-adducts of toluene diisocyanate, trimethylol propane-adducts of xylylene diisocyanate, and combinations thereof.

The second microcapsule contains a second oil core and a second microcapsule wall encapsulating the second oil core. The second microcapsule wall is formed of a second encapsulating polymer, which can be selected from the group consisting of melamine-formaldehyde polymers, polyureas, polyurethanes, gelatins, urea formaldehyde polymers, sol gel polymers, starch polymers, carbohydrates, polyureas (prepared from polyvinyl alcohol as a dispersant) and combinations thereof. In some preferred embodiments, the second encapsulating polymer is the reaction product of a polyisocyanate and hexamethylenediamine. The polyisocyanate is defined above.

The first and second oil cores, respectively, contain a first and second active materials, which are, independently, selected from the group consisting of a fragrance, pro-fragrance, flavor, vitamin or derivative thereof, malodor counteractive agent, anti-inflammatory agent, fungicide, anesthetic, analgesic, antimicrobial active, anti-viral agent, anti-infectious agent, anti-acne agent, skin lightening agent, insect repellant, emollient, skin moisturizing agent, wrinkle control agent, UV protection agent, fabric softener active, hard surface cleaning active, skin or hair conditioning agent, insect repellant, animal repellent, vermin repellent, flame retardant, antistatic agent, nanometer to micron size inorganic solid, polymeric or elastomeric particle, and combination thereof.

In some embodiments, the microcapsule compositions described above further comprise a deposition aid selected from the group consisting of polyquaternium-4, polyquaternium-5, polyquaternium-6, polyquaternium-7, polyquaternium-10, polyquaternium-16, polyquaternium-22, polyquaternium-24, polyquaternium-28, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, and combinations thereof.

In other embodiments, the microcapsule compositions of this invention further comprise a capsule formation aid selected from the group consisting of a polyvinyl alcohol, polystyrene sulfonate, carboxymethyl cellulose, naphthalene sulfonate, polyvinylpyrrolidone, copolymer of vinyl pyrrolidone and quaternized dinethylaminoethyl methacrylate, and combination thereof.

The microcapsule compositions of this invention can further comprise a third, fourth, fifth, or sixth delivery system.

Any of the microcapsule compositions described above can be in the form of a solid or liquid (e.g., a slurry).

Another aspect of this invention relates to a consumer product containing an above-described microcapsule composition. Examples of the consumer product include a hair care product such as shampoos and hair conditioners, a personal care product such as bar soaps and body washes, a fabric care product (e.g., powder or liquid fabric detergents, fabric conditioners, and fabric refreshers), and a home care product.

The details of one or more embodiments of the invention are set forth in the description below. Other features, objects, and advantages of the invention will be apparent from the description and the claims.

DETAILED DESCRIPTION OF THE INVENTION

It has been found that the capsule performance (e.g., fragrance intensity) is unexpectedly improved when combining in a microcapsule composition a cationic microcapsule (having a zeta potential of 10 mV or greater) with an anionic microcapsule (having a zeta potential of −10 mV or less) or with a neutral microcapsule (having a zeta potential of −5 to 5 mV).

The microcapsule compositions of this invention are useful in a wide range of consumer applications, e.g., personal hair care products including shampoos and hair conditioners; personal washes such as soaps, body wash, personal cleaners, and sanitizers; fabric care such as fabric refreshers, softeners, and dryer sheets; ironing water; industrial cleaners; liquid and powder detergent; rinse conditioners; fine fragrances; an Eau De Toilette product; a deodorant; an roll-on product; and an aerosol product. The capsule compositions of this invention are also well-suited for use in hydroalcoholic medium such as fine fragrance and for use in leave-on personal care applications. Moreover, the inclusion of a capsule formation aid in the capsule wall-forming reaction provides capsules with excellent storage stability and retention of an encapsulated fragrance.

The microcapsule compositions of this invention contain at least two microcapsules, e.g., a first microcapsule and a second microcapsule.

The First Microcapsule

The first microcapsule is a positively charged microcapsule having a zeta potential of 10 mV or greater, preferably 25 mV or greater (e.g., 25 mV to 200 mV), and more preferably 40 mV or greater (e.g., 40 mV to 100 mV). Not to be bound by any theory, these positively charged microcapsules not only have a strong affinity to specific animate and inanimate surfaces, but also immobilize other neutral or negatively charged microcapsules and thus also bind them to the animate and inanimate surfaces.

The first microcapsule can be prepared by reacting (e.g., via an interfacial polymerization) a polyfunctional nucleophile and a polyfunctional electrophile in the presence of a capsule formation aid (e.g., a dispersant) and/or a catalyst (e.g., a base) so that an active material is encapsulated in a first oil core by a first microcapsule wall. The first oil core optionally contains a core modifier. The first microcapsule wall is formed of a first encapsulating polymer that is the reaction product of a polyfunctional nucleophile and a polyfunctional electrophile.

A preferred first microcapsule has a microcapsule wall formed of a first encapsulating polymer that is a reaction product of a branched polyethyleneimine (a polyfunctional nucleophile) and an aromatic/aliphatic polyisocyanate (a polyfunctional electrophile).

Polyfunctional Nucleophiles.

The polyfunctional nucleophiles each are a branched polyethyleneimine or a mixture containing a branched polyethyleneimine and a polyfunctional amine/alcohol. In a preferred embodiment, the polyfunctional nucleophile is a branched polyethyleneimine.

Suitable branched polyethyleneimines each have a molecular weight of 200 to 1,000,000 Da (e.g., 300 to 500,000 Da, 500 to 200,000 Da, 750 to 100,000 Da, and 750 to 50,000 Da). They each have a main chain and one or more side chains attached to the main chain. The main chain has 2 to 25,000 (e.g., 3 to 10,000, 5 to 5000, and 5 to 500) repeat ethylene amine (—CH$_2$CH$_2$NH—) units. The side chains each have one or more ethylene amine terminals (—CH$_2$CH$_2$NH$_2$). The representative structure of the branched polyethyleneimine is shown below:

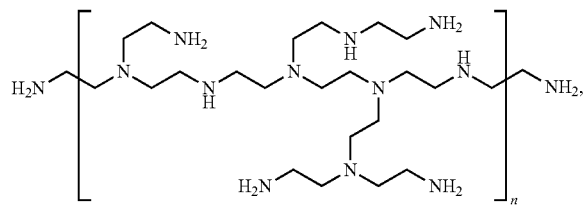

in which n is 1 to 5000 (e.g., 1 to 2000, 1 to 1000, and 1 to 100).

Other suitable polyfunctional nucleophiles include polyfunctional amines (e.g., polyamines) and polyfunctional alcohols (e.g., polyols).

Polyfunctional amines are those having at least a primary/secondary amine group (—NH$_2$ and —NH—) and one or more additional functional groups such as a primary/secondary amine and hydroxyl group (—OH). Exemplary polyfunctional amines include hexamethylenediamine, hexaethylenediamine, ethylenediamine, 1,3-diamino-propane, 1,4-diamino-butane, diethylenetriamine, pentaethylenehexamine, bis(3-amino-propyl)amine, bis(hexanethyl-ene)triamine, tris(2-aminoethyl)amine, triethylene-tetramine, N,N'-bis(3-aminopropyl)-1,3-propanediamine, tetraethylenepentamine, amino-2-methyl-1-propanol, a second branched polyethylenimine, chitosan, 1,3-diamino-guanidine, 1,1-dimethylbiguanide, and guanidine. Suitable amino acids/peptides include arginine, lysine, histidine, ornithine, nisin, and gelatin.

Preferred polyfunctional amines are polyamines containing two or more amine groups such as —NH$_2$ and —R*NH, R* being substituted and unsubstituted C$_1$-C$_{20}$ alkyl, C$_1$-C$_{20}$ heteroalkyl, C$_1$-C$_{20}$ cycloalkyl, 3- to 8-membered heterocycloalkyl, aryl, and heteroaryl.

Two classes of such polyamines include polyalkylene polyamines having the following structures:

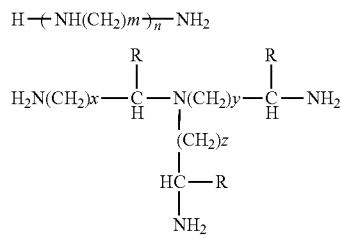

In which R is hydrogen or —CH$_3$; and each of m, n, x, y, and z, independently, is an integer from 0-2000 (e.g., 1-1000, 1-100, 1-10, and 1-5). Examples include ethylene diamine, 1,3-diaminepropane, diethylene triamine, triethylene tetramine, 1,4-diaminobutane, hexanethylene diamine, hexamethylene diamine, pentaethylenehexamine, and the like.

Another class of polyamines are polyalykylene polyamines of the type:

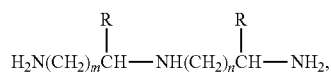

where R equals hydrogen or —CH$_3$, m is 1-5 and n is 1-5, e.g., diethylene triamine, triethylene tetraamine and the like. Exemplary amines of this type also include diethylenetriamine, bis(3-aminopropyl)amine, bis(hexanethylene)triamine.

Another class of amine that can be used in the invention is polyetheramines. They contain primary amino groups attached to the end of a polyether backbone. The polyether backbone is normally based on either propylene oxide (PO), ethylene oxide (EO), or mixed PO/EO. The ether amine can be monoamine, diamine, or triamine, based on this core structure. An example is:

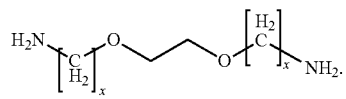

Additional examples include 2,2'-ethylenedioxy)bis (ethylamine) and 4,7,10-trioxa-1,13-tridecanediamine.

Other suitable amines include, but are not limited to, tris(2-aminoethyl)amine, triethylenetetramine, N,N'-bis(3-aminopropyl)-1,3-propanediamine, tetraethylene pentamine, 1,2-diaminopropane, N,N,N',N'-tetrakis(2-hydroxyethyl)ethylene diamine, N,N,N',N'-tetrakis(2-hydroxypropyl)ethylene diamine, branched polyethylenimine, 2,4-diamino-6-hydroxypyrimidine and 2,4,6-triaminopyrimidine.

Amphoteric amines, i.e., amines that can react as an acid as well as a base, are another class of amines of use in this invention. Examples of amphoteric amines include proteins and amino acids such as gelatin, L-lysine, D-lysine, L-arginine, D-arginine, L-lysine monohydrochloride, D-lysine monohydrochloride, L-arginine monohydrochloride, D-arginine monohydrochloride, L-ornithine monohydrochloride, D-ornithine monohydrochloride or a mixture thereof.

Guanidine amines and guanidine salts are yet another class of multi-functional amines of use in this invention. Exemplary guanidine amines and guanidine salts include, but are not limited to, 1,3-diaminoguanidine monohydrochloride, 1,1-dimethylbiguanide hydrochloride, guanidine carbonate and guanidine hydrochloride.

Commercially available examples of amines include JEFFAMINE EDR-148 (where x=2), JEFFAMINE EDR-176 (where x=3) (from Huntsman). Other polyether amines include the JEFFAMINE ED Series, JEFFAMINE TRIAMINES, polyethylenimines from BASF (Ludwigshafen, Germany) under LUPASOL grades (e.g., Lupasol FG, Lupasol G20 waterfree, Lupasol PR 8515, Lupasol WF, Lupasol FC, Lupasol G20, Lupasol G35, Lupasol G100, Lupasol G500, Lupasol HF, Lupasol PS, Lupasol HEO 1, Lupasol PN50, Lupasol PN60, Lupasol PO100 and Lupasol SK). Other commercially available polyethylenimines include EPOMIN P-1000, EPOMIN P-1050, EPOMIN RP18W and EPOMIN PP-061 from NIPPON SHOKUBAI (New York, N.Y.). Polyvinylamines such as those sold by BASF under LUPAMINE grades can also be used. A wide range of polyetheramines may be selected by those skilled in the art. In certain embodiments, the polyfunctional nucleophile is hexamethylene diamine, polyetheramine or a mixture thereof.

The structures of specific polyfunctional nucleophiles are shown in Table 1 below.

TABLE 1

Exemplary Polyfunctional Nucleophiles

H₂N−NH−CH₂CH₂−NH₂
Diethylenetriamine (H₂N−CH₂CH₂)₃N
Tris(2-aminoethyl)amine

H(NHCH₂CH₂)₅NH₂
Pentaethylenehexamine

H₂N−C(=NH)−NH−NH₂ · HCl
1,3-Diaminoguanidine monohydrochloride

H₂N−C(=NH)−N(CH₃)₂ · HCl (biguanide structure)
1,1-Dimethylbiguanide hydrochloride H₂N−(CH₂)₃−NH−(CH₂)₃−NH₂
Bis(3-aminopropyl)amine H₂N−(CH₂)₆−NH−(CH₂)₆−NH₂
Bis(hexanethylene)triamine H₂N−CH₂CH₂−NH−CH₂CH₂−NH−CH₂CH₂−NH₂
Triethylenetetramine H₂N−(CH₂)₃−NH−(CH₂)₃−NH−(CH₂)₃−NH₂
N,N'-Bis(3-aminopropyl)-1,3-propanediamine H₂N−CH₂CH₂−NH−CH₂CH₂−NH−CH₂CH₂−NH−CH₂CH₂−NH₂
Tetraethylenepentamine TABLE 1-continued Exemplary Polyfunctional Nucleophiles Branched Polyethylenimine Chitosan Guanidine carbonate TABLE 1-continued
Exemplary Polyfunctional Nucleophiles
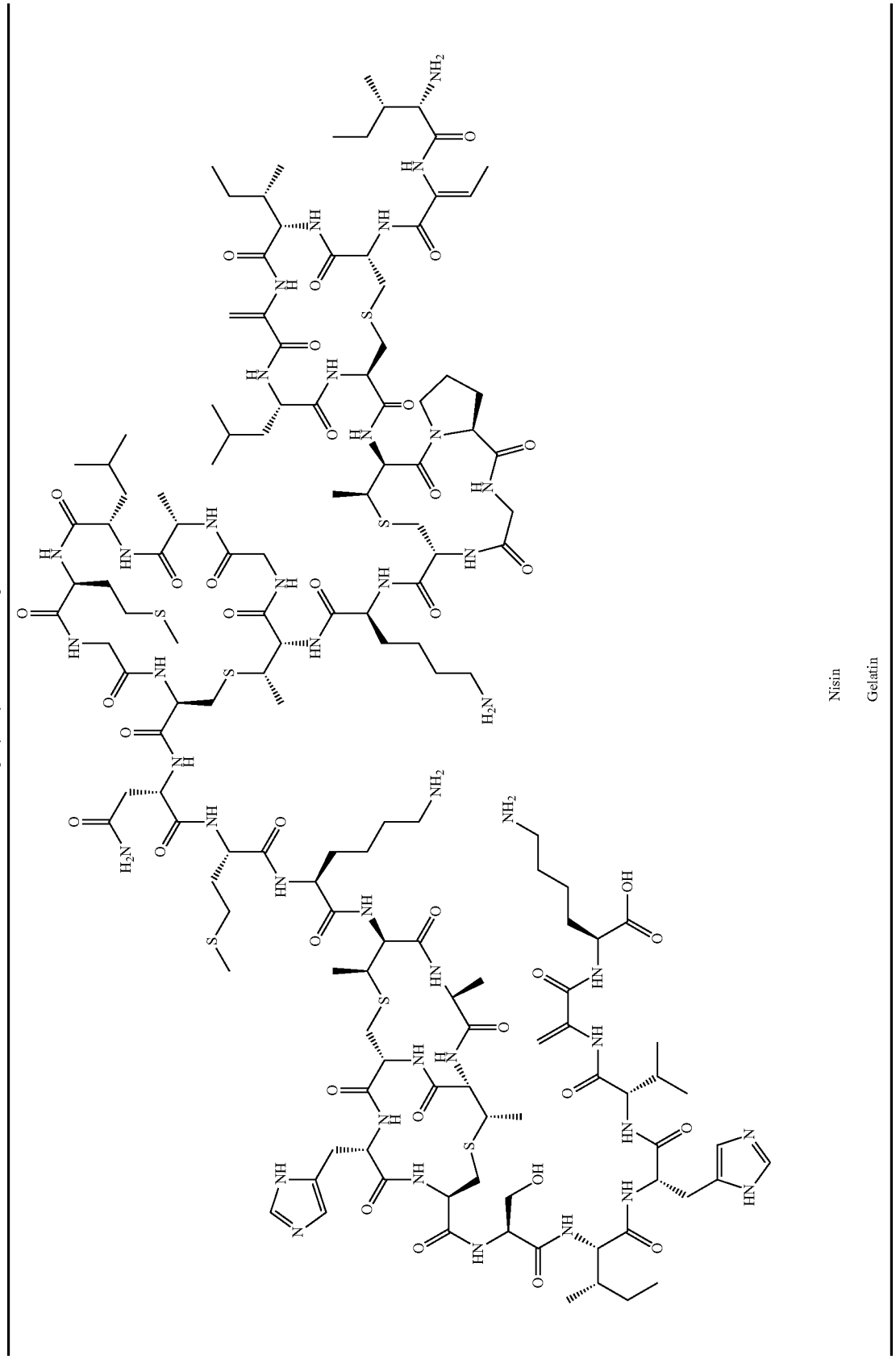
Nisin
Gelatin Polyfunctional alcohols are those having two or more hydroxyl groups. Non-limiting examples are pentaerythritol, glucose, 2-aminoethanol, dipentaerythritol, glycerol, polyglycerol, ethylene glycol, hexylene glycol, polyethylene glycol, trimethylolpropane, neopentyl glycol, sorbitol, erythritol, threitol, arabitol, xylitol, ribitol, mannitol, galactitol, fucitol, iditol, inositol, volemitol, isomalt, maltitol, lactitol, maltotriitol, maltotetraitol, polyglycitol, and combinations thereof. More suitable polyfunctional alcohols are described in WO 2015/023961.

The polyfunctional nucleophile as used in this invention can be a single compound (e.g., a branched polyethyleneimine) or a mixture of a branched polyethyleneimine with one or more polyfunctional amines/alcohols.

The range of polyfunctional nucleophile content can vary from 0.05 to 5% (e.g., 0.1 to 3%, 0.1 to 2%, 0.25 to 2%, and 0.25 to 1%) by weight of the microcapsule composition of this invention.

In one embodiment, the polyfunctional nucleophile is added to the polymerization reaction at a temperature of 0-55° C. (e.g., 10-50° C., 15-45° C., 20-40° C., and 22-35° C.).

Polyfunctional Electrophiles.

The polyfunctional electrophiles each have at least two electrophilic functional groups reactive towards the branched polyethyleneimine, the polyfunctional amine, or the polyfunctional alcohol to form a network of the first encapsulating polymer. Examples of the electrophilic group include formyl, keto, carboxyl, an isocyanate group, a carboxylate ester group, an acyl halide group, an amide group, a carboxylic anhydride group, an alkyl halide group, an epoxide group, an aziridine group, an oxetane group, an azetidine group, a sulfonyl halide group, a chlorophosphate group, an α,β-unsaturated carbonyl group, an α,β-unsaturated nitrile group, a trifluoromethanesulfonate group, a p-toluenesulfonate group, and an α,β-unsaturated methanesulfonyl group.

Suitable polyfunctional electrophiles include glutaric dialdehyde, succinic dialdehyde, and glyoxal; as well as compounds such as glyoxyl trimer and paraformaldehyde, bis(dimethyl) acetal, bis(diethyl) acetal, polymeric dialdehydes, such as oxidized starch. Preferably the cross-linking agent is a low molecular weight, difunctional aldehyde, such as glyoxal, 1,3-propane dialdehyde, 1,4-butane dialdehyde, 1,5-pentane dialdehyde, or 1,6-hexane.

Other non-limiting polyfunctional electrophiles are polyfunctional isocyanates (i.e., polyisocyanate), each of which contains two or more isocyanate (—NCO) groups. These polyisocyanate can be aromatic, aliphatic, linear, branched, or cyclic. In certain embodiments, the polyisocyanate contains, on average, 2 to 4 isocyanate groups. In particular embodiments, the polyisocyanate contains at least three isocyanate functional groups. In certain embodiments, the polyisocyanate is water insoluble.

In particular embodiments, the polyisocyanate used in this invention is an aromatic polyisocyanate. Desirably, the aromatic polyisocyanate includes a phenyl, tolyl, xylyl, naphthyl or diphenyl moiety as the aromatic component. In certain embodiments, the aromatic polyisocyanate is a polyisocyanurate of toluene diisocyanate, a trimethylol propane-adduct of toluene diisocyanate or a trimethylol propane-adduct of xylylene diisocyanate.

One class of suitable aromatic polyisocyanates are those having the generic structure shown below, and its structural isomers

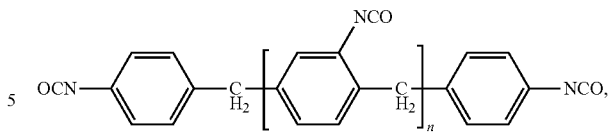

wherein n can vary from zero to a desired number (e.g., 0-50, 0-20, 0-10, and 0-6) depending on the type of polyamine or polyol used. Preferably, the number of n is limited to less than 6. The starting polyisocyanate may also be a mixture of polyisocyanates where the value of n can vary from 0 to 6. In the case where the starting polyisocyanate is a mixture of various polyisocyanates, the average value of n preferably falls in between 0.5 and 1.5. Commercially-available polyisocyanates include LUPRANATE M20 (PMDI, commercially available from BASF containing isocyanate group "NCO" 31.5 wt %), where the average n is 0.7; PAPI 27 (PMDI commercially available from Dow Chemical having an average molecular weight of 340 and containing NCO 31.4 wt %) where the average n is 0.7; MONDUR MR (PMDI containing NCO at 31 wt % or greater, commercially available from Bayer) where the average n is 0.8; MONDUR MR Light (PMDI containing NCO 31.8 wt %, commercially available from Bayer) where the average n is 0.8; MONDUR 489 (PMDI commercially available from Bayer containing NCO 30-31.4 wt %) where the average n is 1; poly[(phenylisocyanate)-co-formaldehyde](Aldrich Chemical, Milwaukee, Wis.), other isocyanate monomers such as DESMODUR N3200 (poly(hexamethylene diisocyanate) commercially available from Bayer), and TAKENATE D110-N (xylene diisocyanate adduct polymer commercially available from Mitsui Chemicals corporation, Rye Brook, N.Y., containing NCO 11.5 wt %), DESMODUR L75 (a polyisocyanate base on toluene diisocyanate commercially available from Bayer), and DESMODUR IL (another polyisocyanate based on toluene diisocyanate commercially available from Bayer).

The structures of certain commercially available polyisocyanates of the invention are shown below:

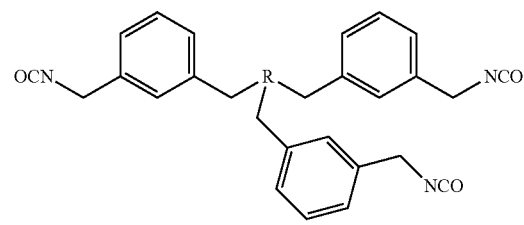

or its structural isomer. R can be a $C_1$-$C_{10}$ alkyl, $C_1$-$C_{10}$ ester, or an isocyanurate. Representative polyisocyanates having this structure are TAKENATE D-110N (Mitsui), DESMODUR L75 (Bayer), and DESMODUR IL (Bayer).

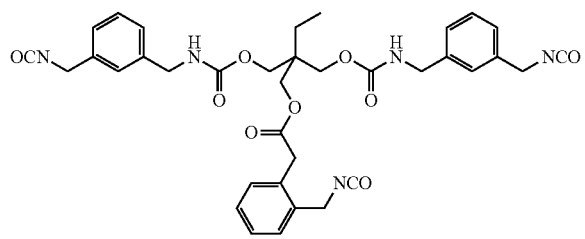

TAKENATE D-110N

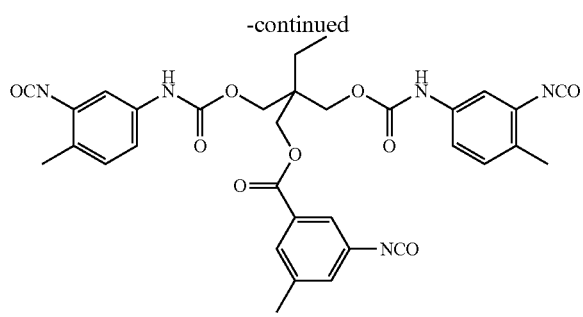

DESMODUR L75

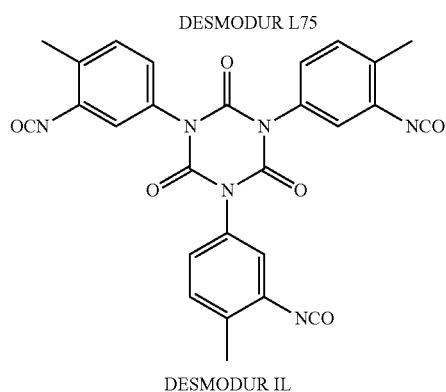

DESMODUR IL

Other specific examples of wall monomer isocyanates include 1,5-naphthylene diisocyanate, 4,4'-diphenylmethane diisocyanate (MDI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), 4,4'-diisocyanatophenylperfluoroethane, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, and 3,3-bis-chloromethyl ether 4,4'-diphenyldiisocyanate, and combinations thereof.

In other embodiments, the polyisocyanate is an aliphatic polyisocyanate. In certain embodiments, the aliphatic polyisocyanate is a trimer of hexamethylene diisocyanate, a trimer of isophorone diisocyanate or a biuret of hexamethylene diisocyanate. Exemplary aliphatic polyisocyanates include those commercially available, e.g., BAYHYDUR N304 and BAYHYDUR N305, which are aliphatic water-dispersible polyisocyanates based on hexamethylene diisocyanate; DESMODUR N3600, DESMODUR N3700, and DESMODUR N3900, which are low viscosity, polyfunctional aliphatic polyisocyanates based on hexamethylene diisocyanate; and DESMODUR 3600 and DESMODUR N100 which are aliphatic polyisocyanates based on hexamethylene diisocyanate, each of which is available from Bayer Corporation, Pittsburgh, Pa.). More examples include 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethyl-cyclohexane, chlorinated and brominated diisocyanates, phosphorus-containing diisocyanates, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, and combinations thereof. Sulfur-containing polyisocyanates are obtained, for example, by reacting hexamethylene diisocyanate with thiodiglycol or dihydroxydihexyl sulfide. Further suitable diisocyanates are trimethylhexamethylene diisocyanate, 1,4-diisocyanatobutane, 1,2-diisocyanatododecane, dimer fatty acid diisocyanate, and combinations thereof.

The average molecular weight of certain polyisocyanates useful in this invention varies from 250 to 1000 Da and preferable from 275 to 500 Da. In general, the range of the polyisocyanate concentration in the composition of this invention varies from 0.1 to 10%, preferably from 0.1 to 8%, more preferably from 0.2 to 5%, and even more preferably from 1.5 to 3.5%, all based on the total capsule composition.

In some embodiments, the polyfunctional isocyanate used in the preparation of the capsules of this invention is a single polyisocyanate. In other embodiments the polyisocyanate is a mixture of polyisocyanates. In some embodiments, the mixture of polyisocyanates includes an aliphatic polyisocyanate and an aromatic polyisocyanate. In particular embodiments, the mixture of polyisocyanates is a biuret of hexamethylene diisocyanate and a trimethylol propane-adduct of xylylene diisocyanate. In certain embodiments, the polyisocyanate is an aliphatic isocyanate or a mixture of aliphatic isocyanate, free of any aromatic isocyanate. In other words, in these embodiments, no aromatic isocyanate is used to prepare the polyurea/polyurethane polymers as capsule wall materials.

More examples of suitable isocyanates can be found in PCT 2004/054362; EP 0 148149; EP 0 017 409 B1; U.S. Pat. Nos. 4,417,916, 4,124,526, 5,583,090, 6,566,306, 6,730,635, PCT 90/08468, PCT WO 92/13450, U.S. Pat. Nos. 4,681,806, 4,285,720 and 6,340,653.

Capsule Formation Aids.

The first microcapsule is typically prepared in the presence of a capsule formation aid, which can be a surfactant or dispersant. Not to be bound by any theory, capsule formation aids improve the performance of the microcapsule composition. Performance is measured by the intensity of the fragrance release during the pre-rub and post-rub phases. The pre-rub phase is the phase when the capsules have been deposited on the cloth, e.g., after a fabric softener containing capsules has been used during the wash cycle. The post-rub phase is after the capsules have been deposited and the capsules are broken by friction or other similar mechanisms.

In some embodiments, the capsule formation aid is a protective colloid or emulsifier including, e.g., maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide and ethylene oxide, polyvinylpyrrolidone (PVP), polyvinyl alcohols (PVA), sodium salt of naphthalene sulfonate condensate, carboxymethyl cellulose (CMC), fatty acid esters of polyoxyethylenated sorbitol, sodium dodecylsulfate, and any combination thereof. In general, the range of surfactant concentration in the capsule composition varies from 0.1 to 5% (e.g., 0.5 to 4%, 0.2 to 2%, and 1 to 2%).

Commercially available surfactants include, but are not limited to, sulfonated naphthalene-formaldehyde condensates such as MORWET D425 (naphthalene sulfonate, Akzo Nobel, Fort Worth, Tex.); partially hydrolyzed polyvinyl alcohols such as MOWIOLs, e.g., MOWIOL 3-83 (Air Products); ethylene oxide-propylene oxide block copolymers or poloxamers such as PLURONIC, SYNPERONIC or PLURACARE materials (BASF); sulfonated polystyrenes such as FLEXAN II (Akzo Nobel); ethylene-maleic anhydride polymers such as ZEMAC (Vertellus Specialties Inc.); and Polyquaternium series such as Polyquaternium 11

("PQ11;" a copolymer of vinyl pyrrolidone and quaternized dimethylaminoethyl methacrylate; sold by BASF as LUVIQUAT PQ11 AT 1).

Processing aids can also be used as capsule formation aids. They include hydrocolloids, which improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful in the present invention include, but are not limited to, polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly(alkyl(meth)acrylate-co-(meth)acrylic acid), poly(acrylic acid-co-maleic acid)copolymer, poly(alkyleneoxide), poly(vinyl-methylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), and the like, and their quaternized forms.

The capsule formation aid may also be used in combination with CMC and/or a surfactant during processing to facilitate capsule formation. Examples of surfactants that can be used in combination with the capsule formation aid include, but are not limited to, cetyl trimethyl ammonium chloride (CTAC), poloxamers such as PLURONICS (e.g., PLURONIC F127), PLURAFAC (e.g., PLURAFAC F127), or MIRANET-N, saponins such as QNATURALE (National Starch Food Innovation); or a gum Arabic such as Seyal or Senegal. The amount of surfactant present in the capsule slurry can vary depending on the surfactant used. In some embodiments the amount of surfactant is in the range of 0.05 to 0.2% by weight of the capsule compositions, in particular when CTAC is employed. In another embodiment, the amount of surfactant is in the range of 1 to 3%.

When combined with CMC, a lighter color PVA is preferred. According to the invention, the CMC polymer may be represented by the following structure:

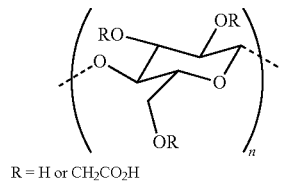

R = H or CH₂CO₂H

In certain embodiments, the CMC polymer has a molecular weight range between 90,000 to 1,500,000 Da, preferably between 250,000 to 750,000 Da, and more preferably between 400,000 to 750,000 Da. The CMC polymer has a degree of substitution between 0.1 to 3, preferably between 0.65 to 1.4, and more preferably between 0.8 to 1.

The carboxymethyl cellulose polymer is present in the capsule slurry at a level from 0.1 to 2% and preferably from 0.3 to 0.7%.

In some embodiments, capsules formed in presence of a capsule aid may unexpectedly provide a perceived fragrance intensity increase of greater than 15%, and preferably an increase of greater than 25% as compared to capsules formed without a capsule formation aid.

Catalysts.

Catalysts suitable for use in the invention are metal carbonates, metal hydroxide, amino or organometallic compounds and include, for example, sodium carbonate, cesium carbonate, potassium carbonate, lithium hydroxide, 1,4-diazabicyclo[2.2.2]octane (i.e., DABCO), N,N-dimethylaminoethanol, N,N-dimethylcyclohexylamine, bis-(2-dimethylaminoethyl) ether, N,N dimethylacetylamine, stannous octoate and dibutyltin dilaurate.

The Second Microcapsule

The second microcapsule can be any of the microcapsules described above but different to the first microcapsule in term of the microcapsule size, the degree of polymerization, the degree of crosslinking, the encapsulating polymer, the thickness of the wall, the active material, the ratio between the wall material and the active material, the zeta potential, the rupture force or fracture strength, and the like.

In some other embodiments, the second microcapsule has a second microcapsule wall different from that of the first microcapsule. The second microcapsule wall can be formed of a second encapsulating polymer selected from the group consisting of sol-gel polymer (e.g., silica), polyacrylate, polyacrylamide, poly(acrylate-co-acrylamide), polyurea, polyurethane, starch, gelatin and gum Arabic, poly (melamine-formaldehyde), poly(urea-formaldehyde), and combinations thereof.

These encapsulating polymers are described in detail below.

Sol-Gel Microcapsules.

These microcapsules have a microcapsule wall formed of a sol-gel polymer, which is a reaction product of a sol-gel precursor via a polymerization reaction (e.g., hydrolyzation). Suitable sol-gel precursors are compounds capable of forming gels such as compounds containing silicon, boron, aluminum, titanium, zinc, zirconium, and vanadium. Preferred precursors are organosilicon, organoboron, and organoaluminum including metal alkoxides and b-diketonates.

Sol-gel precursors suitable for the purposes of the invention are selected in particular from the group of di-, tri- and/or tetrafunctional silicic acid, boric acid and alumoesters, more particularly alkoxysilanes (alkyl orthosilicates), and precursors thereof.

One example of sol-gel precursors suitable for the purposes of the invention are alkoxysilanes corresponding to the following general formula:

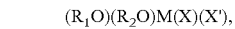

(R₁O)(R₂O)M(X)(X'), wherein X can be hydrogen or —OR₃; X' can be hydrogen or —OR₄; and R₁, R₂, R₃ and R₄ independently represent an organic group, more particularly a linear or branched alkyl group, preferably a C₁-C₁₂ alkyl. M can be Si, Ti, or Zr.

A preferred sol/gel precursor is alkoxysilanes corresponding to the following general formula: (R₁O)(R₂O)Si(X)(X'), wherein each of X, X', R₁, and R₂ are defined above.

Particularly preferred compounds are the silicic acid esters such as tetramethyl orthosilicate (TMOS) and tetraethyl orthosilicate (TEOS). A preferred compound includes Dynasylan® (organofunctional silanes commercially available from Degussa Corporation, Parsippany N.J., USA). Other sol-gel precursors suitable for the purposes of the invention are described, for example, in German Patent Application DE10021165. These sol-gel precursors are various hydrolyzable organosilanes such as, for example, alkylsilanes, alkoxysilanes, alkyl alkoxysilanes and organoalkoxysilanes. Besides the alkyl and alkoxy groups, other organic groups (for example allyl groups, aminoalkyl groups, hydroxyalkyl groups, etc.) may be attached as substituents to the silicon.

Recognizing that metal and semi metal alkoxide monomers (and their partially hydrolyzed and condensed polymers) such as tetramethoxy silane (TMOS), tetraethoxy silane (TEOS), etc. are very good solvents for numerous molecules and active ingredients is highly advantageous since it facilitates dissolving the active materials at a high concentration and thus a high loading in the final capsules.

Polyaciylate Microcapsules, Polyaciylamide Microcapsules, and poly(acylate-co-acrylamide) Microcapsules.

Each of these microcapsules is prepared from a corresponding precursor. Preferred precursors are bi- or polyfunctional vinyl monomers including by way of illustration and not limitation, allyl methacrylate/acrylamide, triethylene glycol dimethacrylate/acrylamide, ethylene glycol dimethacrylate/acrylamide, diethylene glycol dimethacrylate/acrylamide, triethylene glycol dimethacrylate/acrylamide, tetraethylene glycol dimethacrylate/acrylamide, propylene glycol dimethacrylate/acrylamide, glycerol dimethacrylate/acrylamide, neopentyl glycol dimethacrylate/acrylamide, 1,10-decanediol dimethacrylate/acrylamide, pentaerythritol trimethacrylate/acrylamide, pentaerythritol tetramethacrylate/acrylamide, dipentaerythritol hexamethacrylate/acrylamide, triallyl-formal trimethacrylate/acrylamide, trimethylol propane trimethacrylate/acrylamide, tributanediol dimethacrylate/acrylamide, aliphatic or aromatic urethane diacrylates/acrylamides, difunctional urethane acrylates/acrylamides, ethoxylated aliphatic difunctional urethane methacrylates/acrylamides, aliphatic or aromatic urethane dimethacrylates/acrylamides, epoxy acrylates/acrylamides, epoxymethacrylates/acrylamides, 1,3-butylene glycol diacrylate/acrylamide, 1,4-butanediol dimethacrylate/acrylamide, 1,4-butaneidiol diacrylate/acrylamide, diethylene glycol diacrylate/acrylamide, 1,6-hexanediol diacrylate/acrylamide, 1,6-hexanediol dimethacrylate/acrylamide, neopentyl glycol diacrylate/acrylamide, polyethylene glycol diacrylate/acrylamide, tetraethylene glycol diacrylate/acrylamide, triethylene glycol diacrylate/acrylamide, 1,3-butylene glycol dimethacrylate/acrylamide, tripropylene glycol diacrylate/acrylamide, ethoxylated bisphenol diacrylate/acrylamide, ethoxylated bisphenol dimethylacrylate/acrylamide, dipropylene glycol diacrylate/acrylamide, alkoxylated hexanediol diacrylate/acrylamide, alkoxylated cyclohexane dimethanol diacrylate/acrylamide, propoxylated neopentyl glycol diacrylate/acrylamide, trimethylol-propane triacrylate/acrylamide, pentaerythritol triacrylate/acrylamide, ethoxylated trimethylolpropane triacrylate/acrylamide, propoxylated trimethylolpropane triacrylate/acrylamide, propoxylated glyceryl triacrylate/acrylamide, ditrimethyloipropane tetraacrylate/acrylamide, dipentaerythritol pentaacrylate/acrylamide, ethoxylated pentaerythritol tetraacrylate/acrylamide, PEG 200 dimethacrylate/acrylamide, PEG 400 dimethacrylate/acrylamide, PEG 600 dimethacrylate/acrylamide, 3-acryloyloxy glycol monoacrylate/acrylamide, triacryl formal, triallyl isocyanate, and triallyl isocyanurate.

The monomer is polymerized in the presence of an activation agent (e.g., an initiator) at a raised temperature (e.g., 30-90° C.) or under UV light. Exemplary initiators are 2,2'-azobis(isobutyronitrile) ("AIBN"), dicetyl peroxydicarbonate, di(4-tert-butylcyclohexyl) peroxydicarbonate, dioctanoyl peroxide, dibenzoyl peroxide, dilauroyl peroxide, didecanoyl peroxide, tert-butyl peracetate, tert-butyl perlaurate, tert-butyl perbenzoate, tert-butyl hydroperoxide, cumene hydroperoxide, cumene ethylperoxide, diisopropylhydroxy dicarboxylate, 2,2'-azobis(2,4-dimethyl valeronitrile), 1,1'-azobis(cyclohexane-1-carbonitrile), dimethyl 2,2'-azobis(2-methylpropionate), 2,2'-azobis[2-methyl-N-(2-hydroxyethyl) propionamide, sodium persulfate, benzoyl peroxide, and combinations thereof.

Emulsifiers used in the formation of polyacrylate/polyacrylamide/poly(acrylate-co-acrylamide) capsule walls are typically anionic emulsifiers including by way of illustration and not limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates. The amount of anionic emulsifier is anywhere from 0.1 to 40 percent by weight of all constituents, more preferably from 0.5 to 10 percent, more preferably 0.5 to 5 percent by weight.

Aminoplasts and Gelatin.

A representative process used for aminoplast encapsulation is disclosed in U.S. Pat. No. 3,516,941 and US 2007/0078071, though it is recognized that many variations with regard to materials and process steps are possible. Another encapsulation process, i.e., gelatin encapsulation, is disclosed in U.S. Pat. No. 2,800,457. Both processes are discussed in the context of fragrance encapsulation for use in consumer products in U.S. Pat. Nos. 4,145,184 and 5,112,688 respectively. Polymer systems are well-known in the art and non-limiting examples of these include aminoplast capsules and encapsulated particles as disclosed in GB 2006709 A; the production of micro-capsules having walls comprising styrene-maleic anhydride reacted with melamine-formaldehyde precondensates as disclosed in U.S. Pat. No. 4,396,670; an acrylic acid-acrylamide copolymer, cross-linked with a melamine-formaldehyde resin as disclosed in U.S. Pat. No. 5,089,339; capsules composed of cationic melamine-formaldehyde condensates as disclosed in U.S. Pat. No. 5,401,577; melamine formaldehyde microencapsulation as disclosed in U.S. Pat. No. 3,074,845; amido-aldehyde resin in-situ polymerized capsules disclosed in EP 0 158 449 A1; etherified urea-formaldehyde polymer as disclosed in U.S. Pat. No. 5,204,185; melamine-formaldehyde microcapsules as described in U.S. Pat. No. 4,525,520; cross-linked oil-soluble melamine-formaldehyde precondensate as described in U.S. Pat. No. 5,011,634; capsule wall material formed from a complex of cationic and anionic melamine-formaldehyde precondensates that are then cross-linked as disclosed in U.S. Pat. No. 5,013,473; polymeric shells made from addition polymers such as condensation polymers, phenolic aldehydes, urea aldehydes or acrylic polymer as disclosed in U.S. Pat. No. 3,516,941; urea-formaldehyde capsules as disclosed in EP 0 443 428 A2; melamine-formaldehyde chemistry as disclosed in GB 2 062 570 A; and capsules composed of polymer or copolymer of styrene sulfonic acid in acid of salt form, and capsules cross-linked with melamine-formaldehyde as disclosed in U.S. Pat. No. 4,001,140.

Urea-Formaldehyde and Melamine-Formaldehyde Capsules.

Urea-formaldehyde and melamine-formaldehyde precondensate capsule shell wall precursors are prepared by means of reacting urea or melamine with formaldehyde where the mole ratio of melamine or urea to formaldehyde is in the range of from 10:1 to 1:6, preferably from 1:2 to 1:5. For purposes of practicing this invention, the resulting material has a molecular weight in the range of from 156 to 3000. The resulting material may be used 'as-is' as a cross-linking agent for the aforementioned substituted or un-substituted acrylic acid polymer or copolymer or it may be further reacted with a $C_1$-$C_6$ alkanol, e.g., methanol, ethanol, 2-propanol, 3-propanol, 1-butanol, 1-pentanol or 1-hexanol, thereby forming a partial ether where the mole ratio of melamine/urea:formaldehyde:alkanol is in the range of 1:(0.1-6):(0.1-6). The resulting ether moiety-containing product may be used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or co-polymers. Methods for formation of such melamine-formaldehyde and urea-formaldehyde pre-condensates are set forth in U.S. Pat. Nos. 3,516,846 and 6,261,483, and Lee et al. (2002) J. Microencapsulation 19, 559-569.

Examples of urea-formaldehyde pre-condensates useful in the practice of this invention are URAC 180 and URAC 186, trademarks of Cytec Technology Corp. of Wilmington, Del. Examples of melamine-formaldehyde pre-condensates useful in the practice if this invention, include, but are not limited to, CYMEL U-60, CYMEL U-64 and CYMEL U-65, trademarks of Cytec Technology Corp. of Wilmington, Del. It is preferable to use, as the precondensate for cross-linking, the substituted or un-substituted acrylic acid polymer or co-polymer. In practicing this invention, the range of mole ratios of urea-formaldehyde precondensate/melamine-formaldehyde pre-condensate to substituted/un-substituted acrylic acid polymer/co-polymer is in the range of from 9:1 to 1:9, preferably from 5:1 to 1:5 and most preferably from 2:1 to 1:2.

In one embodiment of the invention, microcapsules with polymer(s) composed of primary and/or secondary amine reactive groups or mixtures thereof and cross-linkers can also be used. See US 2006/0248665. The amine polymers can possess primary and/or secondary amine functionalities and can be of either natural or synthetic origin. Amine-containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable amine polymers are the LUPAMIN series of polyvinyl formamides available from BASF. The molecular weights of these materials can range from 10,000 to 1,000,000 Da.

Urea-formaldehyde or melamine-formaldehyde capsules can also include formaldehyde scavengers, which are capable of binding free formaldehyde. When the capsules are for use in aqueous media, formaldehyde scavengers such as sodium sulfite, melamine, glycine, and carbohydrazine are suitable. When the capsules are aimed to be used in products having low pH, e.g., fabric care conditioners, formaldehyde scavengers are preferably selected from beta diketones, such as beta-ketoesters, or from 1,3-diols, such as propylene glycol. Preferred beta-ketoesters include alkylmalonates, alkyl aceto acetates and polyvinyl alcohol aceto acetates.

The microcapsule composition of this invention optionally contains one or more additional microcapsules, e.g., a third, fourth, fifth, or sixth microcapsules. Each of these microcapsules can be any of the microcapsule described above.

Active Materials

The core of the capsules of the invention can include one or more active materials including, but not limited to, flavors and/or fragrance ingredients such as fragrance oils. Individual perfume ingredients that can be encapsulated include:

i) hydrocarbons, such as, for example, 3-carene, α-pinene, β-pinene, α-terpinene, γ-terpinene, p-cymene, bisabolene, camphene, caryophyllene, cedrene, farnesene, limonene, longifolene, myrcene, ocimene, valencene, (E,Z)-1,3,5-undecatriene, styrene, and diphenylmethane;

ii) aliphatic alcohols, such as, for example, hexanol, octanol, 3-octanol, 2,6-dimethyl-heptanol, 2-methyl-2-heptanol, 2-methyl-2-octanol, (E)-2-hexenol, (E)- and (Z)-3-hexenol, 1-octen-3-ol, a mixture of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, 4-methyl-3-decen-5-ol, aliphatic aldehydes and their acetals such as for example hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal-diethylacetal, 1,1-dimethoxy-2,2,5-trimethyl-4-hexene, and citronellyl oxyacetaldehyde;

iii) aliphatic ketones and oximes thereof, such as, for example, 2-heptanone, 2-octanone, 3-octanone, 2-nonanone, 5-methyl-3-heptanone, 5-methyl-3-heptanone oxime, 2,4,4,7-tetra-methyl-6-octen-3-one, aliphatic sulfur-containing compounds, such as for example 3-methylthio-hexanol, 3-methylthiohexyl acetate, 3-mercaptohexanol, 3-mercaptohexyl acetate, 3-mercapto-hexyl butyrate, 3-acetylthiohexyl acetate, 1-menthene-8-thiol, and aliphatic nitriles (e.g., 2-nonenenitrile, 2-tridecenenitrile, 2,12-tridecenenitrile, 3,7-dimethyl-2,6-octadienenitrile, and 3,7-dimethyl-6-octenenitrile);

iv) aliphatic carboxylic acids and esters thereof, such as, for example, (E)- and (Z)-3-hexenylformate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexylbutyrate, (E)- and (Z)-3-hexenyl isobutyrate, hexyl crotonate, ethylisovalerate, ethyl-2-methyl pentanoate, ethyl hexanoate, allyl hexanoate, ethyl heptanoate, allyl heptanoate, ethyl octanoate, ethyl-(E,Z)-2,4-decadienoate, methyl-2-octinate, methyl-2-noninate, allyl-2-isoamyl oxyacetate, and methyl-3,7-dimethyl-2,6-octadienoate;

v) acyclic terpene alcohols, such as, for example, citronellol, geraniol, nerol, linalool, lavandulol, nerolidol, farnesol, tetrahydrolinalool, tetrahydrogeraniol, 2,6-dimethyl-7-octen-2-ol, 2,6-dimethyloctan-2-ol, 2-methyl-6-methylene-7-octen-2-ol, 2,6-dimethyl-5,7-octadien-2-ol, 2,6-dimethyl-3,5-octadien-2-ol, 3,7-dimethyl-4,6-octadien-3-ol, 3,7-dimethyl-1,5,7-octatrien-3-ol, 2,6-dimethyl-2,5,7-octatrien-1-ol, as well as formates, acetates, propionates, isobutyrates, butyrates, isovalerates, pentanoates, hexanoates, crotonates, tiglinates and 3-methyl-2-butenoates thereof;

vi) acyclic terpene aldehydes and ketones, such as, for example, geranial, neral, citronellal, 7-hydroxy-3,7-dimethyloctanal, 7-methoxy-3,7-dimethyloctanal, 2,6,10-trimethyl-9-undecenal, α-sinensal, β-sinensal, geranylacetone, as well as the dimethyl- and diethylacetals of geranial, neral and 7-hydroxy-3,7-dimethyloctanal;

vii) cyclic terpene alcohols, such as, for example, menthol, isopulegol, alpha-terpineol, terpinen-4-ol, menthan-8-ol, menthan-1-ol, menthan-7-ol, borneol, isoborneol, linalool oxide, nopol, cedrol, ambrinol, vetiverol, guaiol, and the formates, acetates, propionates, isobutyrates, butyrates, isovalerates, pentanoates, hexanoates, crotonates, tiglinates and 3-methyl-2-butenoates of alpha-terpineol, terpinen-4-ol, methan-8-ol, methan-1-ol, methan-7-ol, borneol, isoborneol, linalool oxide, nopol, cedrol, ambrinol, vetiverol, and guaiol;

viii) cyclic terpene aldehydes and ketones, such as, for example, menthone, isomenthone, 8-mercaptomenthan-3-one, carvone, camphor, fenchone, α-ionone, β-ionone, α-n-methylionone, β-n-methylionone, α-isomethylionone, β-isomethylionone, alpha-irone, α-damascone, β-damascone, β-damascenone, δ-damascone, γ-damascone, 1-(2,4,4-trimethyl-2-cyclohexen-1-yl)-2-buten-1-one, 1,3,4,6,7,8a-hexahydro-1,1,5,5-tetra-methyl-2H-2,4a-methanonaphthalen-8(5H-)-one, nootkatone, dihydronootkatone; acetylated cedarwood oil (cedryl methyl ketone);

ix) cyclic alcohols, such as, for example, 4-tert-butylcyclohexanol, 3,3,5-trimethylcyclohexanol, 3-isocamphylcyclohexanol, 2,6,9-trimethyl-Z2,Z5,E9-cyclo-dodecatrien-1-ol, 2-iso-butyl-4-methyltetrahydro-2H-pyran-4-ol;

x) cycloaliphatic alcohols, such as, for example, alpha, 3,3-trimethylcyclo-hexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, 1-(2,2,6-trimethylcyclohexyl)hexan-3-ol;

xi) cyclic and cycloaliphatic ethers, such as, for example, cineole, cedryl methyl ether, cyclododecyl methyl ether;

xii) (ethoxymethoxy)cyclododecane; alpha-cedrene epoxide, 3a,6,6,9a-tetramethyl-dodecahydronaphtho[2,1-b]furan, 3a-ethyl-6,6,9a-trimethyldodecahydro-naphtho[2,1-b]furan, 1,5,9-trimethyl-13-oxabicyclo[10.1.0]-trideca-4,8-diene, rose oxide, 2-(2,4-dimethyl-3-cyclohexen-1-yl)-5-methyl-5-(1-methylpropyl)-1,3-dioxan-;

xiii) cyclic ketones, such as, for example, 4-tert.-butyl-cyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetra-methylcyclohexanone, 4-tert.-pentylcyclohexanone, 5-cyclohexadecen-1-one, 6,7-dihydro-1,1,2,3,3-pentamethyl-4(5H)-indanone, 5-cyclohexadecen-1-one, 8-cyclohexa-decen-1-one, 9-cycloheptadecen-1-one, cyclopentadecanone, cycloaliphatic aldehydes, such as, for example, 2,4-dimethyl-3-cyclohexene carbaldehyde, 2-methyl-4-(2,2,6-trimethyl-cyclohexen-1-yl)-2-butenal, 4-(4-hydroxy-4-methylpentyl)-3-cyclohexene carbaldehyde, 4-(4-methyl-3-penten-1-yl)-3-cyclohexene carbaldehyde;

xiv) cycloaliphatic ketones, such as, for example, 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphtalenyl methyl-ketone, methyl-2,6,10-trimethyl-2,5,9-cyclododecatrienyl ketone, tert.-butyl-(2,4-dimethyl-3-cyclohexen-1-yl)ketone;

xv) esters of cyclic alcohols, such as, for example, 2-tert.-butylcyclohexyl acetate, 4-tert-butylcyclohexyl acetate, 2-tert-pentylcyclohexyl acetate, 4-tert-pentyl-cyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl-isobutyrate, 4,7-methanooctahydro-5 or 6-indenyl acetate;

xvi) esters of cycloaliphatic carboxylic acids, such as, for example, allyl 3-cyclohexyl-propionate, allyl cyclohexyl oxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, ethyl 2-methyl-1,3-dioxolane-2-acetate;

xvii) aromatic and aliphatic alcohols, such as, for example, benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)-propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol;

xviii) esters of aliphatic alcohols and aliphatic carboxylic acids, such as, for example, benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, α-trichloromethylbenzyl acetate, α,α-dimethyl-phenylethyl acetate, alpha, alpha-dimethylphenylethyl butyrate, cinnamyl acetate, 2-phenoxyethyl isobutyrate, 4-methoxybenzyl acetate, araliphatic ethers, such as for example 2-phenylethyl methyl ether, 2-phenylethyl isoamyl ether, 2-phenylethyl-1-ethoxyethyl ether, phenylacetaldehyde dimethyl acetal, phenylacetaldehyde diethyl acetal, hydratropaaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, 4,4a,5,9b-tetrahydro-2,4-dimethylindeno[1,2-d]-m-dioxin;

xix) aromatic and aliphatic aldehydes, such as, for example, benzaldehyde; phenylacet-aldehyde, 3-phenylpropanal, hydratropaldehyde, 4-methylbenzaldehyde, 4-methylphenyl-acetaldehyde, 3-(4-ethylphenyl)-2,2-dimethylpropanal, 2-methyl-3-(4-iso-propylphenyl)propanal, 2-methyl-3-(4-tert.-butylphenyl)propanal, 3-(4-tert.-butyl-phenyl) propanal, cinnamaldehyde, alpha-butylcinnamaldehyde, alpha-amylcinnam-aldehyde, alpha-hexylcinnamaldehyde, 3-methyl-5-phenylpentanal, 4-methoxy-benzaldehyde, 4-hydroxy-3-methoxybenzaldehyde, 4-hydroxy-3-ethoxybenzaldehyde, 3,4-methylene-dioxybenzaldehyde, 3,4-dimethoxybenzaldehyde, 2-methyl-3-(4-methoxyphenyl)propanal, 2-methyl-3-(4-methylendioxyphenyl)propanal;

xx) aromatic and aliphatic ketones, such as, for example, acetophenone, 4-methylacetophenone, 4-methoxyacetophenone, 4-tert.-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert.-butyl-1,1-dimethyl-4-indanyl methyl ketone, 1-[2,3-dihydro-1,1,2,6-tetramethyl-3-(1-methyl-ethyl)-1H-5-indenyl]ethanone, 5',6',7',8'-tetrahydro-3',5',5',6',8',8'-hexamethyl-2-acetonaphthone;

xxi) aromatic and araliphatic carboxylic acids and esters thereof, such as, for example, benzoic acid, phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate;

xxii) nitrogen-containing aromatic compounds, such as, for example, 2,4,6-trinitro-1,3-dimethyl-5-tert-butylbenzene, 3,5-dinitro-2,6-dimethyl-4-tert-butylaceto-phenone, cinnamonitrile, 5-phenyl-3-methyl-2-pentenonitrile, 5-phenyl-3-methylpentano-nitrile, methyl anthranilate, methy-N-methylanthranilate, Schiff's bases of methyl anthranilate with 7-hydroxy-3,7-dimethyl-octanal, 2-methyl-3-(4-tert.-butylphenyl)-propanal or 2,4-dimethyl-3-cyclohexene carbaldehyde, 6-isopropylquinoline, 6-isobutyl-quinoline, 6-sec-butylquinoline, indole, skatole, 2-methoxy-3-isopropylpyrazine, 2-isobutyl-3-methoxypyrazine;

xxiii) phenols, phenyl ethers and phenyl esters, such as, for example, estragole, anethole, eugenol, eugenyl methyl ether, isoeugenol, isoeugenol methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate;

xxiv) heterocyclic compounds, such as, for example, 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

xxv) lactones, such as, for example, 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis- and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene-1,12-dodecanedioate, ethylene-1,13-tridecanedioate, coumarin, 2,3-dihydrocoumarin, and octahydrocoumarin;

xxvi) essential oils, concretes, absolutes, resins, resinoids, balsams, tinctures such as for example ambergris tincture, amyris oil, *angelica* seed oil, *angelica* root oil, aniseed oil, valerian oil, basil oil, tree moss absolute, bay oil, armoise oil, benzoe resinoid, bergamot oil, beeswax absolute, birch tar oil, bitter almond oil, savory oil, buchu leaf oil, cabreuva oil, cade oil, calamus oil, camphor oil, *cananga* oil, cardamom oil, cascarilla oil, *cassia* oil, cassie absolute, castoreum absolute, cedar leaf oil, cedar wood oil, cistus oil, citronella oil, lemon oil, copaiba balsam, copaiba balsam oil, coriander oil, costus root oil, cumin oil, cypress oil, davana oil, dill weed oil, dill seed oil, eau de brouts absolute, oalmnoss absolute, elemi oil, estragon oil, *eucalyptus citriodora* oil, *eucalyptus* oil (cineole type), fennel oil, fir needle oil, *galbanum* oil, *galbanum* resin, geranium oil, grapefruit oil, guaiacwood oil, gurjun balsam, gurjun balsam oil, helichrysum absolute, helichrysum oil, ginger oil, iris root absolute, iris root oil, jasmine absolute, calamus oil, blue camomile oil, Roman camomile oil, carrot seed oil, cascarilla oil, pine needle oil, spearmint oil, caraway oil, labdanum oil, labdanum absolute, labdanum resin, lavandin absolute, lavandin oil, lavender absolute, lavender oil, lemon-grass oil, lovage oil, lime oil distilled, lime oil expressed, linaloe oil, *Litsea cubeba* oil, laurel leaf oil, mace oil, marjoram oil, mandarin oil, massoi (bark) oil, *mimosa* absolute, ambrette seed oil, musk tincture, clary sage oil, nutmeg oil, myrrh absolute, myrrh oil, myrtle oil, clove leaf oil, clove bud oil, neroli oil, olibanum absolute, olibanum oil, opopanax oil, orange flower absolute, orange oil, *origanum* oil, palmarosa oil, patchouli oil, *perilla* oil, Peru balsam oil, parsley leaf oil, parsley seed oil, petitgrain oil, peppermint oil, pepper oil, pimento oil, pine oil, pennyroyal oil, rose absolute, rosewood oil, rose oil, rosemary oil, Dalmatian sage oil, Spanish sage oil, sandal-wood oil, celery seed oil: spike-lavender oil, star anise oil, storax oil, *tagetes* oil, fir needle oil, tea tree oil, turpentine oil, thyme oil, Tolu balsam, tonka bean absolute, tuberose absolute, vanilla extract, violet leaf absolute, *verbena* oil, vetiver oil, juniperberry oil, wine lees oil, wormwood oil, wintergreen oil, ylang-ylang oil, hyssop oil, civet absolute, cinnamon leaf oil, cinnamon bark oil, and fractions thereof or ingredients isolated therefrom;

(xxvii) flavors including, but are not limited to, acetaldehyde, dimethyl sulfide, ethyl acetate, ethyl propionate, methyl butyrate, and ethyl butyrate. Flavors containing volatile aldehydes or esters include, e.g., cinnamyl acetate, cinnamaldehyde, citral, diethylacetal, dihydrocarvyl acetate, eugenyl formate, and p-methylanisole. Further examples of volatile compounds that may be present in the instant flavor oils include acetaldehyde (apple); benzaldehyde (cherry, almond); cinnamic aldehyde (cinnamon); citral, i.e., alpha citral (lemon, lime); neral, i.e., beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e., trans-2 (berry fruits); tolyl aldehyde (cherry, almond); veratraldehyde (vanilla); 2,6-dimethyl-5-heptenal, i.e., melonal (melon); 2-6-dimethyloctanal (green fruit); and 2-dodecenal (citrus, mandarin); cherry; or grape and mixtures thereof. The composition may also contain taste modulators and artificial sweeteners. As used herein, flavor is understood to include spice oleoresins derived from allspice, basil, *capsicum*, cinnamon, cloves, cumin, dill, garlic, marjoram, nutmeg, paprika, black pepper, rosemary, and turmeric, essential oils, anise oil, caraway oil, clove oil, *eucalyptus* oil, fennel oil, garlic oil, ginger oil, peppermint oil, onion oil, pepper oil, rosemary oil, spearmint oil, citrus oil, orange oil, lemon oil, bitter orange oil, tangerine oil, alliaceous flavors, garlic, leek, chive, and onion, botanical extracts, *arnica* flower extract, chamomile flower extract, hops extract, marigold extract, botanical flavor extracts, blackberry, chicory root, cocoa, coffee, kola, licorice root, rose hips, sarsaparilla root, *sassafras* bark, tamarind and vanilla extracts, protein hydrolysates, hydrolyzed vegetable proteins, meat protein hydrolyzes, milk protein hydrolyzates and compounded flavors both natural and artificial including those disclosed in S. Heath, Source Book of Flavors, Avi Publishing Co., Westport Conn., 1981, pages 149-277. Specific preferred flavor adjuvants include, but are not limited to, the following: anise oil; ethyl-2-methyl butyrate; vanillin; cis-3-heptenol; cis-3-hexenol; trans-2-heptenal; butyl valerate; 2,3-diethyl pyrazine; methylcyclo-pentenolone; benzaldehyde; valerian oil; 3,4-dimeth-oxyphenol; amyl acetate; amyl cinnamate, y-butyryl lactone; furfural; trimethyl pyrazine; phenyl acetic acid; isovaleraldehyde; ethyl maltol; ethyl vanillin; ethyl valerate; ethyl butyrate; cocoa extract; coffee extract; peppermint oil; spearmint oil; clove oil; anethol; cardamom oil; wintergreen oil; cinnamic aldehyde; ethyl-2-methyl valerate; g-hexenyl lactone; 2,4-decadienal; 2,4-heptadienal; methyl thiazole alcohol (4-methyl-5-b-hydroxyethyl thiazole); 2-methyl butanethiol; 4-mercapto-2-butanone; 3-mercapto-2-pentanone; 1-mercapto-2-propane; benzaldehyde; furfural; furfuryl alcohol; 2-mercapto propionic acid; alkyl pyrazine; methyl pyrazine; 2-ethyl-3-methyl pyrazine; tetramethyl pyrazine; polysulfides; dipropyl disulfide; methyl benzyl disulfide; alkyl thiophene; 2,3-dimethyl thiophene; 5-methyl furfural; acetyl furan; 2,4-decadienal; guiacol; phenyl acetaldehyde; b-decalactone; d-limonene; acetoin; amyl acetate; maltol; ethyl butyrate; levulinic acid; piperonal; ethyl acetate; n-octanal; n-pentanal; n-hexanal; diacetyl; monosodium glutamate; monopotassium glutamate; sulfur-containing amino acids, e.g., cysteine; hydrolyzed vegetable protein; 2-methylfuran-3-thiol; 2-methyldihydrofuran-3-thiol; 2,5-dimethylfuran-3-thiol; hydrolyzed fish protein; tetramethyl pyrazine; propylpropenyl disulfide; propylpropenyl trisulfide; diallyl disulfide; diallyl trisulfide; dipropenyl disulfide; dipropenyl trisulfide; 4-methyl-2-[(methylthio)-ethyl]-1,3-dithiolane; 4,5-dimethyl-2-(methylthiomethyl)-1,3-dithiolane; 4-methyl-2-(methylthiomethyl)-1,3-dithiolane, and the flavor ingredients described in U.S. Pat. Nos. 6,110,520 and 6,333,180;

(xxviii) taste masking agents, substances for masking one or more unpleasant taste sensations, in particular a bitter, astringent and/or metallic taste sensation or aftertaste. Examples include lactisol [2O-(4-methoxyphenyl) lactic acid] (cf. U.S. Pat. No. 5,045,336), 2,4-dihydroxybenzoic acid potassium salt (cf. U.S. Pat. No. 5,643,941), ginger extracts (cf. GB 2,380,936), neohesperidine dihydrochalcone (cf. Manufacturing Chemist 2000, July issue, p. 16-17), specific flavones (2-phenylchrom-2-en-4-ones) (cf. U.S. Pat. No. 5,580,545), specific nucleotides, for example cytidine-5'-monophosphates (CMP) (cf. US 2002/0177576), specific sodium salts, such as sodium chloride, sodium citrate, sodium acetate and sodium lactate (cf. Nature, 1997, Vol. 387, p. 563), a lipoprotein of .beta.-lactoglobulin and phosphatidic acid (cf. EPA 635 218), neodiosmine [5,7-dihydroxy-2-(4-methoxy-3-hydroxyphenyl)-7-O-neohesperidosyl-chrom-2-en-4-one] (cf. U.S. Pat. No. 4,154,862), preferably hydroxyflavanones according to EP 1 258 200, in turn preferred in this respect 2-(4-hydroxyphenyl)-5,7-dihydroxychroman-4-one (naringenin), 2-(3,4-dihydroxyphenyl)-5,7-dihydroxychroman-4-one (eriodictyol), 2-(3,4-dihydroxyphenyl)-5-hydroxy-7-methoxychroman-4-one (eriodictyol-7-methylether), 2-(3,4-dihydroxyphenyl)-7-hydroxy-5-methoxychroman-4-one, (eriodictyol-5-methylether) and 2-(4-hydroxy-3-methoxyphenyl)-5,7-dihydroxychroman-4-one (homoerio-dictyol), the (2S)- or (2R)-enantiomers thereof or mixtures thereof as well as the mono- or polyvalent phenolate salts thereof with $Na^+$, $K^+$, $NH^+$, $Ca^{2+}$, $Mg^{2+}$ or $Al^{3+}$ as counter cations or .gamma.-aminobutyric acid (4-aminobutyric acid, as the neutral form ("inner salt") or in the carboxylate or ammonium form) according to WO 2005/09684;

(xxix) taste sensates including hot tasting, salivation-inducing substances, substances causing a warmth or tingling feeling, and cooling active ingredients. Examples of hot tasting and/or salivation-inducing substances and/or substances which cause a feeling of warmth and/or a tingling feeling on the skin or on the mucous membranes and which can be a constituent of the products according to the invention are: capsaicin, dihydrocapsaicin, gingerol, paradol, shogaol, piperine, carboxylic acid-N-vanillylamides, in particular nonanoic acid-N-vanillylamide, pellitorin or spilanthol, 2-nonanoic acid amides, in particular 2-nonanoic acid-N-isobutylamide, 2-nonanoic acid-N-4-hydroxy-3-methoxyphenylamide, alkyl ethers of 4-hydroxy-3-methoxybenzyl alcohol, in particular 4-hydroxy-3-methoxybenzyl-n-butylether, alkyl ethers of 4-acyloxy-3-methoxybenzyl alcohol, in particular 4-acetyloxy-3-methoxybenzyl-n-butylether and 4-acetyloxy-3-methoxybenzyl-n-hexylether, alkyl ethers of 3-hydroxy-4-methoxybenzyl alcohol, alkyl ethers of 3,4-dimethoxybenzyl alcohol, alkyl ethers of 3-ethoxy-4-hydroxybenzyl alcohol, alkyl ethers of 3,4-methylene dioxybenzyl alcohol, (4-hydroxy-3-methoxyphenyl)acetic acid amides, in particular (4-hydroxy-3-methoxyphenyl) acetic acid-N-n-octylamide, vanillomandelic acid alkylamides, ferulic acid-phenethylainides, nicotinaldehyde, methylnicotinate, propylnicotinate, 2-butoxyethylnicotinate, benzylnicotinate, 1-acetoxychavicol, polygodial and isodrimeninol, further preferred cis- and/or trans-pellitorin according to WO 2004/000787 or WO 2004/043906, alkenecarboxylic acid-N-alkylamides according to WO 2005/044778, mandelic acid alkylamides according to WO 03/106404 or alkyloxyalkanoic acid amides according to WO 2006/003210. Examples of preferred hot tasting natural extracts and/or natural extracts which cause a feeling of warmth and/or a tingling feeling on the skin or on the mucous membranes and which can be a constituent of the products according to the invention are: extracts of paprika, extracts of pepper (for example *capsicum* extract), extracts of chili pepper, extracts of ginger roots, extracts of *Aframomum melgueta*, extracts of *Spilanthes-acmella*, extracts of *Kaempferia galangal* or extracts of *Alpinia galanga*. Suitable cooling active ingredients include the following: 1-menthol, d-menthol, racemic menthol, menthone glycerol acetal (trade name: Frescolat® MGA), menthyl lactate (trade name: Frescolat® ML, menthyl lactate preferably being 1-menthyl lactate, in particular 1-menthyl-1-lactate), substituted menthyl-3-carboxamides (for example menthyl-3-carboxylic acid-N-ethylamide), 2-isopropyl-N-2,3-trimethyl-butanamide, substituted cyclohexane carboxamides, 3-menthoxypropane-1,2-diol, 2-hydroxyethyl menthyl carbonate, 2-hydroxypropyl menthyl carbonate, N-acetylglycine menthyl ester, isopulegol, hydroxycarboxylic acid menthyl esters (for example menthyl-3-hydroxybutyrate), monomenthyl succinate, 2-mercaptocyclo-decanone, menthyl-2-pyrrolidin-5-onecarboxylate, 2,3-dihydroxy-p-menthane, 3,3,5-trimethylcyclohexanone glycerol ketal, 3-menthyl-3,6-di- and -trioxaalkanoates, 3-menthyl methoxyacetate and icilin. Cooling active ingredients which are particularly preferred are as follows: 1-menthol, racemic menthol, menthone glycerol acetal (trade name: Frescolat® MGA), menthyl lactate (preferably 1-menthyl lactate, in particular 1-menthyl-1-lactate, trade name: Frescolat® ML), 3-menthoxypropane-1,2-diol, 2-hydroxyethyl menthyl carbonate, 2-hydroxypropyl menthyl carbonate.

(xxx) malodor counteracting agents including an α,β-unsaturated carbonyl compounds including but not limited to those disclosed in U.S. Pat. No. 6,610,648 and EP 2,524,704, amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, isomers of bicyclo[2.2.1]hept-5-ene-2-carboxylic acid, ethyl ester, nano silver, zinc undecenylate, β-naphthyl methyl ether, β-naphthyl ketone, benzyl acetone. They may include mixture of hexahydro-4,7-methanoinden-5-yl propionate and hexahydro-4,7-methanoinden-6-yl propionate; 4-(2,6,6-trimethyl-2-cyclohexen-1-yl)-3-methyl-3-buten-2-one; 3,7-dimethyl-2,6-nonadien-1-nitrile; dodeca-hydro-3 a,6,6,9a-tetramethylnaphtho(2,1-b)furan; ethylene glycol cyclic ester of n-dodecanedioic acid; 1-cyclohexadecen-6-one; 1-cycloheptadecen-10-one; and corn mint oil. They may also include 1-cyclohexylethan-1-yl butyrate; 1-cyclohexylethan-1-yl acetate; 1-cyclohexylethan-1-ol; 1-(4'-methylethyl)cyclohexylethan-1-yl propionate; and 2'-hydroxy-1'-ethyl(2-phenoxy)acetate each of which compound is marketed under the trademark VEILEX by International Flavors & Fragrances Inc. More suitable malodor counteracting agents are polymers containing an α-keto, benzaldehyde, or α,β-unsaturated carbonyl moiety, such as those described in US Application Publications 2012/0294821, 2013/0101544 and 2013/0101545;

(xxxi) vitamins including any vitamin, a derivative thereof and a salt thereof. Examples are as follows: vitamin A and its analogs and derivatives (e.g., retinol, retinal, retinyl palmitate, retinoic acid, tretinoin, and iso-tretinoin, known collectively as retinoids), vitamin E (tocopherol and its derivatives), vitamin C (L-ascorbic acid and its esters and other derivatives), vitamin B3 (niacinamide and its derivatives), alpha hydroxy acids (such as glycolic acid, lactic acid, tartaric acid, malic acid, citric acid, etc.) and beta hydroxy acids (such as salicylic acid and the like);

(xxxii) antibacterials including bisguanidines (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol), triclosan (i.e., 2, 4, 4'-trichloro-2' hydroxy-diphenylether), thymol, and triclocarban;

(xxxiii) sunscreen actives including oxybenzone, octylmethoxy cinnamate, butylmethoxy dibenzoyln ethane, p-aminobenzoic acid and octyl dimethyl-p-aminobenzoic acid;

(xxxiv) antioxidants such as beta-carotene, vitamin C (Ascorbic Acid) or an ester thereof, vitamin A or an ester thereof, vitamin E or an ester thereof, lutein or an ester thereof, lignan, lycopene, selenium, flavonoids, vitamin-like antioxidants such as coenzyme Q10 (CoQ10) and glutathione, and antioxidant enzymes such as superoxide dismutase (SOD), catalase, and glutathione peroxidase;

(xxxv) anti-inflammatory agents including, e.g., methyl salicylate, aspirin, ibuprofen, and naproxen. Additional anti-inflammatories useful in topical applications include corticosteroids, such as, but not limited to, flurandrenolide, clobetasol propionate, halobetasol propionate, fluticasone propionate, betamethasone dipropionate, betamethasone benzoate, betamethasone valerate, desoximethasone, dexamethasone, diflorasone diacetate, mometasone furoate, amcinodine, halcinonide, fluocinonide, fluocinolone acetonide, desonide, triamcinolone acetonide, hydrocortisone, hydrocortisone acetate, fluorometholone, methylprednisolone, and predinicarbate;

(xxxvi) anesthetics that can be delivered locally including benzocaine, butamben, butamben picrate, cocaine, procaine, tetracaine, lidocaine and pramoxine hydrochloride;

(xxxvii) analgesics such as ibuprofen, diclofenac, capsaicin, and lidocaine;

(xxxviii) antifungal agents. Non-limiting examples are micanazole, clotrimazole, butoconazole, fenticonasole, tioconazole, terconazole, sulconazole, fluconazole, haloprogin, ketonazole, ketoconazole, oxinazole, econazole, itraconazole, torbinafine, nystatin and griseofulvin;

(xxxix) antibiotics such as erythromycin, clindamycin, synthomycin, tetracycline, metronidazole and the like;

(xl) anti-viral agents including famcyclovir, valacyclovir and acyclovir;

(xli) anti-parasitic agents such as scabicedes, such as permethrin, crotamiton, lindane and ivermectin;

(xlii) anti-infectious and anti-acne agents including benzoyl peroxide, sulfur, resorcinol and salicylic acid;

(xliii) dermatological active ingredients useful in topical applications including, e.g., jojoba oil and aromatic oils such as methyl salicylate, wintergreen, peppermint oil, bay oil, *eucalyptus* oil and citrus oils, as well as ammonium phenolsulfonate, bismuth subgallate, zinc phenolsulfonate and zinc salicylate;

(xliv) enzymes and co-enzymes useful for topical application including co-enzyme Q10, papain enzyme, lipases, proteases, superoxide dismutase, fibrinolysin, desoxyribonuclease, trypsin, collagenase and sutilains;

(xlv) skin whitening agents such as hydroquinone and monobenzone;

(xlvi) anti-histamines including chlorpheniramine, brompheniramine, dexchlorpheniramine, tripolidine, clemastine, diphenhydramine, prometazine, piperazines, piperidines, astemizole, loratadine and terfonadine;

(xlvii) chemotherapeutic agents such as 5-fluorouracil, masoprocol, mechlorethamine, cyclophosphamide, vincristine, chlorambucil, streptozocin, methotrexate, bleomycin, dactinomycin, daunorubicin, coxorubicin and tamoxifen; and (xlviii) insect repellents including pediculicides for treatment of lice, such as pyrethrins, permethrin, malathion, lindane and the like.

In addition to the active materials listed above, the products of this invention can also contain, for example, the following dyes, colorants or pigments: lactoflavin (riboflavin), beta-carotene, riboflavin-5'-phosphate, alpha-carotene, gamma-carotene, cantaxanthin, erythrosine, curcumin, quinoline yellow, yellow orange S, tartrazine, bixin, norbixin (annatto, orlean), capsanthin, capsorubin, lycopene, beta-apo-8'-carotenal, beta-apo-8'-carotenic acid ethyl ester, xantophylls (flavoxanthin, lutein, cryptoxanthin, rubixanthin, violaxanthin, rodoxanthin), fast carmine (carminic acid, cochineal), azorubin, cochineal red A (Ponceau 4 R), beetroot red, betanin, anthocyanins, amaranth, patent blue V, indigotine I (indigo-carmine), chlorophylls, copper compounds of chlorophylls, acid brilliant green BS (lissamine green), brilliant black BN, vegetable carbon, titanium dioxide, iron oxides and hydroxides, calcium carbonate, aluminum, silver, gold, pigment rubine BK (lithol rubine BK), methyl violet B, victoria blue R, victoria blue B, acilan brilliant blue FFR (brilliant wool blue FFR), naphthol green B, acilan fast green 10 G (alkali fast green 10 G), ceres yellow GRN, sudan blue II, ultramarine, phthalocyanine blue, phthalocayanine green, fast acid violet R. Further naturally obtained extracts (for example paprika extract, black carrot extract, red cabbage extract) can be used for coloring purposes. Good results are also achieved with the colors named in the following, the so-called aluminum lakes: FD & C Yellow 5 Lake, FD & C Blue 2 Lake, FD & C Blue 1 Lake, Tartrazine Lake, Quinoline Yellow Lake, FD & C Yellow 6 Lake, FD & C Red 40 Lake, Sunset Yellow Lake, Carmoisine Lake, Amaranth Lake, Ponceau 4R Lake, Erythrosyne Lake, Red 2G Lake, Allura Red Lake, Patent Blue V Lake, Indigo Carmine Lake, Brilliant Blue Lake, Brown HT Lake, Black PN Lake, Green S Lake and mixtures thereof.

When the active material is a fragrance, it is preferred that fragrance ingredients within a fragrance having a C log P of 0.5 to 15 are employed. For instance, the ingredients having a C log P value between 0.5 to 8 (e.g., 1 to 12, 1.5 to 8, 2 to 7, 1 to 6, 2 to 6, 2 to 5, and 3 to 7) are 25% or greater (e.g., 50% or greater and 90% or greater) by the weight of the fragrance.

In some embodiments, it is preferred that a fragrance having a weight-averaged C log P of 2.5 and greater (e.g., 3 or greater, 2.5 to 7, and 2.5 to 5) is employed. The weight-averaged C log P is calculated as follows:

$$C \log P = \{Sum[(Wi)(C \log P)i]\}/\{Sum Wi\},$$

in which Wi is the weight fraction of each fragrance ingredient and (C log P)i is the C log P of that fragrance ingredient.

In certain embodiments, it is preferred that greater than 60 weight percent, preferably greater than 80 and more preferably greater than 90 weight percent of the fragrance chemicals have C log P values of greater than 2, preferably greater than 3.3, more preferably greater than 4, and even more preferably greater than 4.5.

In other embodiments, the ingredients having a C log P value between 2 and 7 (e.g., between 2 and 6, and between 2 and 5) are 25% or greater (e.g., 50% or greater and 90% or greater) by the weight of the fragrance. In still other embodiments, it is preferred that greater than 60%, preferably greater than 80% and more preferably greater than 90% of the fragrance chemicals have Clog P values of greater than 3.3, preferably greater than 4 and most preferably greater than 4.5.

Those with skill in the art will appreciate that many fragrances can be created employing various solvents and fragrance chemicals. The use of a relatively low to intermediate C log P fragrance ingredients will result in fragrances that are suitable for encapsulation. These fragrances are generally water-insoluble, to be delivered through the capsule systems of this invention onto consumer products in different stages such as damp and dry fabric. Without encapsulation, the free fragrances would normally have evaporated or dissolved in water during use, e.g., wash. Though high log P materials are generally well delivered from a regular (non-encapsulated) fragrance in a consumer product, they have excellent encapsulation properties and are also suitable for encapsulation for overall fragrance character purposes, very long-lasting fragrance delivery, or overcoming incompatibility with the consumer product, e.g., fragrance materials that would otherwise be instable, cause thickening or discoloration of the product or otherwise negatively affect desired consumer product properties.

In some embodiments, the amount of encapsulated active material is from 5 to 95% (e.g., 20 to 90% and 40 to 85%) by weight of the capsule. The amount of the capsule wall is from 0.5 to 25% (e.g., 1.5 to 15% and 2.5 to 10%) also by weight of the capsule. In other embodiments, the amount of the encapsulated active material is from 15 to 99.5% (e.g., 50 to 98% and 30 to 95%) by weight of the capsule, and the amount of the capsule wall is from 0.5 to 85% (e.g., 2 to 50% and 5 to 70%) by weight of the capsule.

Adjunct Materials

In addition to the active materials, the present invention also contemplates the incorporation of adjunct materials (i.e., adjuvant) including solvent, emollients, and core modifier materials in the core encapsulated by the capsule wall. Other adjunct materials are solubility modifiers, density modifiers, stabilizers, viscosity modifiers, pH modifiers, or any combination thereof. These modifiers can be present in the wall or core of the capsules, or outside the capsules in delivery system. Preferably, they are in the core as a core modifier.

The one or more adjunct material may be added in the amount of from 0.01 to 25% (e.g., from 0.5 to 10%) by weight of the capsule.

(i) Solvent. Preferable solvent materials are hydrophobic and miscible with the active materials. Solvents increase the compatibility of various active materials, increase the overall hydrophobicity of the mixture containing the active materials, influence the vapor pressure, or serve to structure the mixture. Suitable solvents are those having reasonable affinity for the active materials and a C log P greater than 2.5, preferably greater than 3.5 and more preferably greater than 5.5. In some embodiments, the solvent is combined with the active materials that have C log P values as set forth above. It should be noted that selecting a solvent and active material with high affinity for each other will result in improvement in stability. Exemplary solvents are triglyceride oil, mono and diglycerides, mineral oil, silicone oil, diethyl phthalate, polyalpha olefins, castor oil, isopropyl myristate, mono-, di- and tri-esters and mixtures thereof, fatty acids, and glycerine. The fatty acid chain can range from $C_4$-$C_{26}$ and can have any level of unsaturation. For instance, one of the following solvents can be used: capric/caprylic triglyceride known as NEOBEE M5 (Stepan Corporation); the CAPMUL series by Abitec Corporation (e.g., CAPMUL MCM); isopropyl myristate; fatty acid esters of polyglycerol oligomers, e.g., $R^2CO$—$[OCH_2$—$CH(OCOR^1)$—$CH^2O$—$]_n$, where $R^1$ and $R^2$ can be H or $C_4$-$C_{26}$ aliphatic chains, or mixtures thereof, and n ranges between 2 and 50, preferably 2 and 30; nonionic fatty alcohol alkoxylates like the NEODOL surfactants by BASF; the dobanol surfactants by Shell Corporation or the BIO-SOFT surfactants by Stepan, wherein the alkoxy group is ethoxy, propoxy, butoxy, or mixtures thereof and said surfactants can be end-capped with methyl groups in order to increase their hydrophobicity; di- and tri-fatty acid chain containing nonionic, anionic and cationic surfactants, and mixtures thereof; fatty acid esters of polyethylene glycol, polypropylene glycol, and polybutylene glycol, or mixtures thereof; polyalphaolefins such as the EXXONMOBIL PURESYM PAO line; esters such as the EXXONMOBTL PURESYN esters; mineral oil; silicone oils such polydimethyl siloxane and polydimethylcyclosiloxane; diethyl phthalate; di-octyl adipate and di-isodecyl adipate. In certain embodiments, ester oils have at least one ester group in the molecule. One type of common ester oil useful in the present invention are the fatty acid mono and polyesters such as cetyl octanoate, octyl isonanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like. A second type of useful ester oil is predominantly composed of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives provided they are liquids. Proprietary ester blends such as those sold by FINETEX as FINSOLV are also suitable, as is ethylhexanoic acid glyceride. A third type of ester oil is liquid polyester formed from the reaction of a dicarboxylic acid and a diol. Examples of polyesters suitable for the present invention are the polyesters marketed by EXXONMOBIL under the trade name PURESYN ESTER.

While the core can be free of the solvent, it is preferable that the level of solvent is 80 wt % or less, preferably 50 wt % or less (e.g., 0-20 wt %) by weight of the core.

(ii) Triglycerides and modified triglycerides as emollients. These include vegetable oils such as jojoba, soybean, canola, sunflower, safflower, rice bran, avocado, almond, olive, sesame, persic, castor, coconut, and mink oils.

(iii) Ester oils have at least one ester group in the molecule. One type of common ester oil useful in the present invention are the fatty acid mono and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate.

(iv) Ester oil as a liquid polyester formed from the reaction of a dicarboxylic acid and a diol. Examples of polyesters suitable for the present invention are the polyesters marketed by ExxonMobil under the trade name PURESYN ESTER®, hydrophobic plant extracts.

(v) Silicones include, for example, linear and cyclic polydimethylsiloxanes, amino-modified, alkyl, aryl, and alkylaryl silicone oil.

(vi) Low/non-volatile hydrocarbons (vii) Solid materials. Nanoscale solid particulate materials such as those disclosed in U.S. Pat. No. 7,833,960 may also be incorporated into the core and may be selected from, but not limited to, metal or metallic particles, metal alloys, polymer particles, wax particles, inorganic particulates, minerals and clay particles.

The metal particles can be selected from a non-limiting list of main group elements, transition metal and post-transition metal elements including aluminum (Al), silica (Si), Titanium (Ti), chromium (Cr), manganese (Mn), iron (Fe), nickel (Ni), cobalt (Co), copper (Cu), gold (Au), silver (Ag), platinum (Pt) and palladium (Pd).

Polymer particles of any chemical composition and nature are suitable for the present invention as long as their physical dimension falls into the prescribed region and a liquid core is generated. The polymer particles can be selected from a nonlimiting list of polymers and co-copolymer based on polystyrene, polyvinyl acetate, polylactides, polyglycolides, ethylene maleic anhydride copolymer, polyethylene, polypropylene, polyamide, polyimide, polycarbonate, polyester, polyurethane, polyurea, cellulose and cellulose, and combinations and mixture of such polymers.

The inorganic particulate can be selected from a non-limiting list including silica, titanium dioxide ($TiO_2$), zinc oxide (ZnO), $Fe_2O_3$, and other metal oxides such as but not limited to NiO, $Al_2O_3$, SnO, $SnO_2$, $CeO_2$, ZnO, CdO, $RuO_2$, FeO, CuO, AgO, $MnO_2$, as well as other transition metal oxides.

Examples of nanoscaled material include AEROSIL R812, which has a particle size of less than 25 nm according to the specification from the manufacture, Degussa Corp. Other suitable materials from Degussa include, but not limited to, AEROSIL R972, AEROSIL R974, AEROSIL R104, AEROSIL R106, AEROSIL R202, AEROSIL R805, AEROSIL R812, AEROSIL R812S, AEROSIL R816, AEROSIL R7200, AEROSIL R9200, and AEROXIDE TiO2 P25, AEROXIDE T805, AEROXIDE LE1, AEROXIDE LE2, AEROXIDE TiO2 NKT 90, AEROXIDE Alu C805, titanium dioxide PF2, SIPERNAT Dl110, SIPERNAT D-380. The hydrophobic materials from Deguassa Corp. such as including AEROSILE R812 and R972 are especially preferred.

Nanoscaled materials such as UVINUL $TiO_2$ and Z-COTE HP1 manufactured by BASF can also be used as well as and TI-PURE titanium dioxide, TI-PURE R-700, and TI-SELECT. Additional suitable materials include TS-6200 from Dupont and ZEROFREE 516, HUBERDERM 2000 and HUBERDERM 1000 from the J.M. Huber Corporation, Havre De Grace, Md. Silica products such as SYLOID 63, 244, 72, 63FP 244FP, 72FP, SYLOX 15, 2 and Zeolites such as SYLOSIV A3, SYLOSIV A4 and SYLOSIV K300 from Grace Davison can also be used.

(viii) Polymeric core modifiers. Polymeric core modifiers are also contemplated. It has been found that the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion. Polymeric core modifiers include copolymers of ethylene; copolymers of ethylene and vinyl acetate (ELVAX polymers by DOW Corporation); copolymers of ethylene and vinyl alcohol (EVAL polymers by Kuraray); ethylene/acrylic elastomers such as VALNAC polymers by Dupont; polyvinyl polymers, such as polyvinyl acetate; alkyl-substituted cellulose, such as ethyl cellulose (ETHOCEL made by DOW Corporation) and hydroxypropyl celluloses (KLUCEL polymers by Hercules); cellulose acetate butyrate available from Eastman Chemical; polyacrylates (e.g., AMPHOMER, DEMACRYL LT and DERMACRYL 79, made by National Starch and Chemical Company, the AMERHOLD polymers by Amerchol Corporation, and ACUDYNE 258 by ISP Corporation); copolymers of acrylic or methacrylic acid and fatty esters of acrylic or methacrylic acid such as INTELIMER POLYMERS made by Landec Corporation (see also U.S. Pat. Nos. 4,830,855, 5,665,822, 5,783,302, 6,255,367 and 6,492,462); polypropylene oxide; polybutylene oxide of poly(tetrahydrofuran); polyethylene terephthalate; polyurethanes (DYNAM X by National Starch); alkyl esters of poly(methyl vinyl ether); maleic anhydride copolymers, such as the GANTREZ copolymers and OMNIREZ 2000 by ISP Corporation; carboxylic acid esters of polyamines, e.g., ester-terminated polyamides (ETPA) made by Arizona Chemical Company; polyvinyl pyrrolidone (LUVISKOL series of BASF); block copolymers of ethylene oxide, propylene oxide and/or butylenes oxide including, e.g., PLURONIC and SYNPERONIC polymers/dispersants by BASF. Another class of polymers include polyethylene oxide-co-propyleneoxide-co-butylene oxide polymers of any ethylene oxide/propylene oxide/butylene oxide ratio with cationic groups resulting in a net theoretical positive charge or equal to zero (amphoteric). The general structure is:

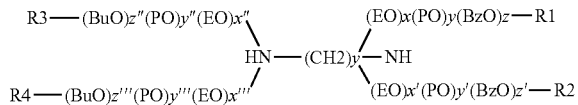

where R1, R2, R3, and R4 are independently H or any alkyl or fatty alkyl chain group. Examples of such polymers are the commercially known as TETRONICS by BASF Corporation.

(ix) Sacrificial core ingredients. These ingredients can also be included in the core and are designed to be lost during or after manufacture and include, but are not limited to, highly water soluble or volatile materials.

(x) Solubility modifiers. Nonlimiting examples of a solubility modifier include surfactants (e.g., SLS and Tween 80), acidic compounds (e.g., mineral acids such as sulfuric acid, hydrochloric acid, nitric acid, and phosphoric acid, and carboxylic acids such as acetic acid, citric acid, gluconic acid, glucoheptonic acid, and lactic acid), basic compounds (e.g., ammonia, alkali metal and alkaline earth metal hydroxides, primary, secondary, or tertiary amines, and primary, secondary, or tertiary alkanolamines), ethyl alcohol, glycerol, glucose, galactose, inositol, mannitol, glactitol, adonitol, arabitol, and amino acids.

(xi) Density modifiers. The density of the capsule slurry and/or the oil core can be adjusted so that the capsule composition has a substantially uniform distribution of the capsules using known density modifiers or technologies such as those described in Patent Application Publications WO 2000/059616, EP 1 502 646, and EP 2 204 155. Suitable density modifiers include hydrophobic materials and materials having a desired molecular weight (e.g., higher than 12,000 Da), such as silicone oils, petrolatums, vegetable oils, especially sunflower oil and rapeseed oil, and hydrophobic solvents having a desired density (e.g., less than 1,000 Kg/m$^3$ at 25° C., such as limonene and octane.

(xii) Stabilizers. In some embodiments, a stabilizer (e.g., a colloidal stabilizer) is added to a capsule delivery system to stabilize the emulsion and/or capsule slurry. Examples of colloidal stabilizers are polyvinyl alcohol, cellulose derivatives such hydroxyethyl cellulose, polyethylene oxide, copolymers of polyethylene oxide and polyethylene or polypropylene oxide, or copolymers of acrylamide and acrylic acid. In other embodiments, a stabilizing agent (i.e., a stabilizer) is added to the capsule delivery system to improve the stability of the delivery system for an extended period of storage. When one of these delivery system is added to a consumer product such as a liquid fabric softener/freshener and liquid detergent, this delivery system will also improve the viscosity stability of the consumer product, thus extend the shelf life of the product.

Useful stabilizing agents include multi-functional amines, amino acids/peptides, mono-functional amines, polymers, and a polymeric mixture. These stabilizing agents are in presence in the compositions as free compounds, which are not covalently attached to the capsule walls, being part of the capsule walls, or encapsulated in capsules.

Multi-functional amines are those having at least an amine group (primary, secondary, or tertiary) and one or more other functional groups such as an amine and hydroxyl group. Exemplary multi-functional amines include hexamethylenediamine, hexaethylenediamine, ethylenediamine, 1,3-diaminopropane, 1,4-diamino-butane, diethylenetriamine, pentaethylenehexamine, bis(3-aminopropyl)amine, bis(hexa-methylene)triamine, tris(2-aminoethyl)amine, triethylene-tetramine, N,N'-bis(3-aminopropyl)-1,3-propanediamine, tetraethylenepentamine, amino-2-methyl-1-propanol branched polyethylenimine, chitosan, 1,3-diaminoguanidine, 1,1-dimethylbiguanide, and guanidine. Suitable amino acids/peptides include arginine, lysine, histidine, ornithine, nisin, and gelatin. Suitable stabilizing polymers include polyvinylpyrrolidone, polyvinylpyridine-N-oxide, and polyvinyl imidazolinium. These polymers sometimes are used in combination with a second polymer (e.g., a block copolymer) such that the second polymer.

Monofunational amines have a single amine group. Examples include C1-C20 primary, secondary, or tertiary amines, each of which typically has a molecular weight of 30 to 800 Da (e.g., 31 to 500 Da and 31 to 300 Da). They can be linear, branched, cyclic, acyclic, saturated, unsaturated, aliphatic, and/or aromatic. Nonlimiting examples are methylamine, dimethylamine, trimethylamine, ethylamine, diethylamine, triethylamine, propylamine, isopropylamine, butylamine, dodecylamine, tetradecylamine, aniline, 4-methylaniline, 2-nitroaniline, diphenyl amine, pyrrolidone, piperidine, and morpholine.

The stabilizing agent in the capsule composition can be present in an amount effective to stabilize the composition and/or the final consumer product containing the composition. This amount can be 1 ppm or greater (e.g., 20 ppm or greater, 20 ppm to 20%, 50 ppm to 10%, 50 ppm to 2%, 50 ppm to 1%, 50 to 2000 ppm, and 50 to 1000 ppm). Its concentration in a consumer product can be 20 ppm to 2% (e.g., 50 ppm to 2%, 50 ppm to 1%, 50 to 2000 ppm, and 50 to 1000 ppm).

(xiii) Viscosity control agents. Viscosity control agents (e.g., suspending agents), which may be polymeric or colloidal (e.g., modified cellulose polymers such as methylcellulose, hydoxyethylcellulose, hydrophobically modified hydroxyethylcellulose, and cross-linked acrylate polymers such as Carbomer, hydrophobically modified polyethers) can be included in the capsule composition, in the capsule core or wall, or in the capsule slurry outside the capsules. Optionally, silicas, either hydrophobic or hydrophilic, can be included at a concentration from 0.01 to 20%, more preferable from 0.5 to 5%, by the weight of the capsule composition. Examples of hydrophobic silicas include silanols, surfaces of which are treated with halogen silanes, alkoxysilanes, silazanes, and siloxanes, such as SIPERNAT D17, AEROSIL R972 and R974 available from Degussa. Exemplary hydrophilic silicas are AEROSIL 200, SIPERNAT 22S, SIPERNAT 50S (available from Degussa), and SYLOID 244 (available from Grace Davison).

(xiv) Humectants. One or more humectants are optionally included to hold water in the capsule composition for a long period of time. Examples include glycerin, propylene glycol, alkyl phosphate esters, quaternary amines, inorganic salts (e.g., potassium polymetaphosphate, sodium chloride, etc.), polyethylene glycols, and the like.

Further suitable humectants, as well as viscosity control/suspending agents, are disclosed in U.S. Pat. Nos. 4,428,869, 4,464,271, 4,446,032, and 6,930,078. Details of hydrophobic silicas as a functional delivery vehicle of active materials other than a free flow/anticaking agent are disclosed in U.S. Pat. Nos. 5,500,223 and 6,608,017.

(xv) pH modifiers. In some embodiments, one or more pH modifiers are included in the capsule composition to adjust the pH value of the capsule slurry and/or the capsule cores. The pH modifiers can also assist in the formation of capsule walls by changing the reaction rate of the crosslinking reactions that form the capsule walls. Exemplary pH modifiers include metal hydroxides (e.g., LiOH, NaOH, KOH, and Mg(OH)$_2$), metal carbonates and bicarbonates (CsCO$_3$ Li$_2$CO$_3$, K$_2$CO$_3$, NaHCO$_3$, and CaCO$_3$), metal phosphates/ hydrogen phosphates/dihydrogen phosphates, metal sulfates, ammonia, mineral acids (HCl, H$_2$SO$_4$, H$_3$PO$_4$, and HNO$_3$), carboxylic acids (e.g., acetic acid, citric acid, lactic acid, benzoic acid, and sulfonic acids), and amino acids.

The level of the adjunct materials can be present at a level of 0.01 to 25% (e.g., from 0.5 to 10%) or greater than 10% (e.g., greater than 30% and greater than 70%).

Deposition Aids

A capsule deposition aid from 0.01 to 25%, more preferably from 5 to 20% can be included by weight of the capsule. The capsule deposition aid can be added during the preparation of the capsules or it can be added after the capsules have been made.

These deposition aids are used to aid in deposition of capsules to surfaces such as fabric, hair or skin. These include anionically, cationically, nonionically, or amphoteric water-soluble polymers. Those skilled in the art would appreciate that the charge of these polymers can be adjusted by changing the pH, depending on the product in which this technology is to be used. Any suitable method for coating the deposition aids onto the encapsulated fragrance materials can be used. The nature of suitable polymers for assisted capsule delivery to interfaces depends on the compatibility with the capsule wall chemistry since there has to be some association to the capsule wall. This association can be through physical interactions, such as hydrogen bonding, ionic interactions, hydrophobic interactions, electron transfer interactions or, alternatively, the polymer coating could be chemically (covalently) grafted to the capsule or particle surface. Chemical modification of the capsule or particle surface is another way to optimize anchoring of the polymer coating to capsule or particle surface. Furthermore, the capsule and the polymer need to be compatible with the chemistry (polarity, for instance) of the desired interface. Therefore, depending on which capsule chemistry and interface (e.g., cotton, polyester, hair, skin, wool), the polymer can be selected from one or more polymers with an overall zero (amphoteric: mixture of cationic and anionic functional groups) or net positive charge, based on the following polymer backbones: polysaccharides, polypeptides, polycarbonates, polyesters, polyolefinic (vinyl, acrylic, acrylamide, poly diene), polyester, polyether, polyurethane, polyoxazoline, polyamine, silicone, polyphosphazine, olyaromatic, poly heterocyclic, or polyionene, with molecular weight (MW) ranging from 1,000 to 1000,000,000 Da, preferably from 5,000 to 10,000,000 Da. As used herein, molecular weight is provided as weight average molecular weight.

Particular examples of cationic polymers that can be used to coat the polyurea or polyurethane capsule include, e.g., polysaccharides such as guar, alginates, starch, xanthan, chitosan, cellulose, dextrans, arabic gum, carrageenan, and hyaluronates. These polysaccharides can be employed with cationic modification and alkoxy-cationic modifications such as cationic hydroxyethyl or cationic hydroxypropyl. For example, cationic reagents of choice are 3-chloro-2-hydroxypropyl trimethylammonium chloride or its epoxy version. Another example is graft-copolymers of polyDAD-MAC on cellulose. Alternatively, polysaccharides can be employed with aldehyde, carboxyl, succinate, acetate, alkyl, amide, sulfonate, ethoxy, propoxy, butoxy, and combinations of these functionalities; or any hydrophobic modification (compared to the polarity of the polysaccharide backbone). The above modifications can be in any ratio and the degree of functionalization can be up to complete substitution of all functionalizable groups, as long as the theoretical net charge of the polymer is zero (mixture of cationic and anionic functional groups) or preferably positive. Furthermore, up to 5 different types of functional groups may be attached to the polysaccharides. Also, polymer graft chains may be differently modified to the backbone. The counterions can be any halide ion or organic counter ion. See U.S. Pat. Nos. 6,297,203 and 6,200,554.

Another source of cationic polymers contain protonatable amine groups so that the overall net charge is zero (amphoteric: mixture of cationic and anionic functional groups) or positive. The pH during use will determine the overall net charge of the polymer. Examples include silk protein, zein, gelatin, keratin, collagen and any polypeptide, such as polylysine.

Further cationic polymers include polyvinyl polymers with up to 5 different types of monomers can be used. The monomers of such polymer have the generic formula:

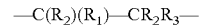

wherein, $R_1$ is H, $C_1$-$C_{25}$ alkane, $C_1$-$C_{25}$ alkene (in which the number of double bonds ranges from 1-5), $C_1$-$C_{25}$ alkoxylated fatty alcohol, or a liquid crystalline moiety that can provide the polymer with thermotropic liquid crystalline properties;

$R_2$ is H or CH$_3$; and $R_3$ is —Cl, —NH$_2$ (i.e., polyvinyl amine or its copolymers with N-vinyl formamide.

Such polyvinyl polymers are sold under the name LUPAMIN 9095 by BASF Corporation. Further suitable cationic polymers containing hydroxylalkylvinylamine units, as disclosed in U.S. Pat. No. 6,057,404.

Another class of materials are polyacrylates with up to 5 different types of monomers. Monomers of polyacrylates have the generic formula:

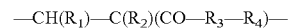

wherein, $R_1$ is H, $C_1$-$C_{25}$ alkane, $C_1$-$C_{25}$ alkene (in which the number of double bonds ranges from 1-5), $C_1$-$C_{25}$ alkoxylated fatty alcohol, or a liquid crystalline moiety that can provide the polymer with thermotropic liquid crystalline properties;

$R_2$ is H or CH$_3$;

$R_3$ is a $C_1$-$C_{25}$ alkyl alcohol or an alkylene oxide with any number of double bonds, or $R_3$ may be absent such that the C=O bond is (via the C-atom) directly connected to $R_4$; and $R_4$ is —NH$_2$, —NHR$_1$, —NR$_1$R$_2$, —NR$_1$R$_2$R$_6$ (where $R_6$=$R_1$, $R_2$, or —CH$_2$—COOH or its salt), —NH—C (O)—, sulfobetaine, betaine, polyethylene oxide, poly(ethyleneoxide/propylene oxide/butylene oxide) grafts with any end group, H, OH, styrene sulfonate, pyridine, quaternized pyridine, alkyl-substituted pyrrolidone or pyridine, pyridine-N-oxide, imidazolinium halide, imidazolium halide, imidazol, piperidine, —OR$_1$, —OH, —COOH alkali salt, sulfonate, ethoxy sulphate, pyrrolidone, caprolactam, phenyl-$R_4$ or naphthalene-$R_5$, where $R_4$ and $R_5$ are $R_1$, $R_2$, $R_3$, sulfonic acid or its alkali salt or organic counter ion. Also, glyoxylated cationic polyacrylamides can be used. Typical polymers of choice are those containing the cationic monomer dimethylaminoethyl methacrylate (DMAEMA) or methacrylamidopropyl trimethyl ammonium chloride (MAPTAC). DMAEMA can be found in GAFQUAT and GAFFIX VC-713 polymers from ISP. MAPTAC can be found in BASF's LUVIQUAT PQ11 PN and ISP's GAF-QUAT HS 100.

Another group of polymers that can be used are those that contain cationic groups in the main chain or backbone. Included in this group are:

i) polyalkylene imines such as polyethylene imine, commercially available as LUPASOL from BASF. Any molecular weight and any degree of crosslinking of this polymer can be used in the present invention;

ii) ionenes as disclosed in U.S. Pat. Nos. 4,395,541 and 4,597,962;

iii) adipic acid/dimethyl amino hydroxypropyl diethylene triamine copolymers, such as CARTARETIN F-4 and F-23, commercially available from Sandoz;

iv) polymers of the general formula: —[N(CH$_3$)$_2$—(CH$_2$)$_x$—NH—(CO)—NH—(CH$_2$)$_y$—N(CH$_3$)$_2$—(CH$_2$)$_z$—O—(—CH$_2$)$_p$]$_n$—, with x, y, z, p=1-12, and n according to the molecular weight requirements. Examples are Polyquaternium-2 (MIRAPOL A-15), Polyquaternium-17 (MIRAPOL AD-1), and Polyquaternium-18 (MIRAPOL AZ-1). Other polymers include cationic polysiloxanes and cationic polysiloxanes with carbon-based grafts with a net theoretical positive charge or equal to zero (mixture of cationic and anionic functional groups). This includes cationic end-group functionalized silicones (i.e., Polyquaternium-80). Silicones with general structure: —Si(R$_1$)(R$_2$)—O—]$_x$—[Si(R$_3$)(R$_2$)—O—]$_y$— where R$_1$ is any alkane from C$_1$-C$_{25}$ or H with number of double bonds from 0-5, aromatic moieties, polysiloxane grafts, or mixtures thereof. R$_1$ can also be a liquid crystalline moiety that can provide the polymer with thermotropic liquid crystalline properties. R$_2$ can be H or CH$_3$; and R$_3$ can be —R$_1$-R$_4$, where R$_4$ can be —NH$_2$, —NHR$_1$, —NR$_1$R$_2$, —NR$_1$R$_2$R$_6$ (where R$_6$=R$_1$, R$_2$, or —CH$_2$—COOH or its salt), —NH—C(O)—, —COOH, —COO— alkali salt, any C$_1$-C$_{25}$ alcohol, —C(O)—NH$_2$ (amide), —C(O)—N(R$_2$)(R$_2$')(R$_2$"), sulfobetaine, betaine, polyethylene oxide, poly(ethyleneoxide/propylene oxide/butylene oxide) grafts with any end group, H, —OH, styrene sulfonate, pyridine, quaternized pyridine, alkyl-substituted pyrrolidone or pyridine, pyridine-N-oxide, imnidazolinium halide, imidazolium halide, imidazol, piperidine, pyrrolidone, caprolactam, sulfonate, ethoxysulphate phenyl-R$_5$ or naphthalene-R$_6$ where R$_5$ and R$_6$ are R$_1$, R$_2$, R$_3$, sulfonic acid or its alkali salt or organic counter ion. R$_3$ can also be —(CH$_2$)$_x$—O—CH$_2$—CH(OH)—CH$_2$—N(CH$_3$)$_2$—CH$_2$—COOH and its salts. Any mixture of these R$_3$ groups can be selected. X and y can be varied as long as the theoretical net charge of the polymer is zero (amphoteric) or positive. In addition, polysiloxanes containing up to 5 different types of monomeric units may be used. Examples of suitable polysiloxanes are found in U.S. Pat. Nos. 4,395,541 4,597,962 and 6,200,554. Another group of polymers that can be used to improve capsule/particle deposition are phospholipids that are modified with cationic polysiloxanes. Examples of these polymers are found in U.S. Pat. No. 5,849,313, WO Patent Application 95/18096A1 and European Patent No. 0737183B1.

Furthermore, copolymers of silicones and polysaccharides and proteins can be used (e.g., those commercially available as CRODASONE brand products).

Another class of polymers includes polyethylene oxide-co-propyleneoxide-co-butylene oxide polymers of any ethylene oxide/propylene oxide/butylene oxide ratio with cationic groups resulting in a net theoretical positive charge or equal to zero (amphoteric). Examples of such polymers are the commercially available TETRONIC brand polymers.

Suitable polyheterocyclic (the different molecules appearing in the backbone) polymers include the piperazine-alkylene main chain copolymers disclosed by Kashiki and Suzuki (1986) *Ind. Eng. Chem. Fundam.* 25:120-125.

Table 2 below shows polyquaternium polymers that can be used as deposition aids in this invention.

TABLE 2

Deposition Aids - Cationic Polyquaternium Polymers

| Polyquaternium | Description | Commercial Products |
|---|---|---|
| 1 | Ethanol, 2,2',2"-nitrilotris-, polymer with 1,4-dichloro-2-butene and N,N,N',N'-tetramethyl-2-butene-1,4-diamine | Polyquad (Alcon) |
| 2 | Poly[bis(2-chloroethyl) ether-alt-1,3-bis[3-(dimethylamino)propyl]urea] | Mirapol A-15 |
| 4 | Hydroxyethyl cellulose dimethyl diallylammonium chloride copolymer; Diallyldimethylammonium chloride-hydroxyethyl cellulose copolymer | Celquat L-200, H-100, L-200 |
| 5 | Copolymer of acrylamide and quaternized dimethylammoniumethyl methacrylate | Merquat 5, RETEN (Hercules) |
| 6 | Poly(diallyldimethylammonium chloride) | Merquat 100, 106, Mirapol 100 |
| 7 | Copolymer of acrylamide and diallyldimethylammonium chloride | Merquat 550, 550L, 550PR, S, 7SPR, 740, 2200, Mirapol 550, Polyquart 770/NA, Conditioneze 7 |
| 8 | Methyl and Stearyl Dimethylaminoethyl Methacrylate Quaternized with Dimethyl Sulfate | |
| 9 | Polydimethylaminoethyl Methacrylate Quaternized with Methyl Bromide | |
| 10 | Quaternized hydroxyethyl cellulose | Merquat 10, Celquat SC-230M, SC-240C, SC-140C, Ucare Polymer |
| 11 | Copolymer of vinylpyrrolidone and quaternized dimethylaminoethyl methacrylate | Luviquat PQ 11PN, Gafquat 775N, 440, 734, 775 |

TABLE 2-continued

Deposition Aids - Cationic Polyquaternium Polymers

| Polyquaternium | Description | Commercial Products |
|---|---|---|
| 12 | 2-Propenoic Acid, 2-Methyl-, Decahydro-1,4-Dimethyl-7-(1-Methylethyl)-1-Phenanthrenyl)Methyl Ester, Polymer with 2-(Diethylamino)Ethyl 2-Methyl-2-Propenoate and Ethyl 2-Methyl-2-Propenoate, compd. with Dimethyl Sulfate | |
| 13 | 2-Propenoic Acid, 2-Methyl-, 2-(Diethyl-amino)Ethyl Ester, Polymer with Ethyl 2-Methyl-2-Propenoate and 9-Octadecenyl 2-Methyl-2-Propenoate, compd. with Dimethyl Sulfate | |
| 14 | Ethanaminium, N,N,N-Trimethyl-2-[(2-Methyl-1-Oxo-2-Propenyl)Oxy]-, Methyl Sulfate, Homopolymer | |
| 15 | Ethanaminium, N,N,N-Trimethyl-2-[(2-Methyl-1-Oxo-2-Propenyl)Oxy]-,Chloride, Polymer with 2-Propenamide | Rohagit KF 720F (Rohm GmbH) |
| 16 | Copolymer of vinylpyrrolidone and quaternized vinylimidazole | Luviquat FC 370, HM 552, Style, FC 550, Excellence |
| 17 | Poly(Oxy-1,2-Ethanediyl (Dimethyl-iminio)-1,3-Propanediylimino(1,6-Dioxo-1,6-Hexanediyl)Imino-1,3-Propanediyl-(Dimethyliminio)-1,2-Ethanediyl Dichloride | Mirapol AD |
| 18 | Poly[oxy-1,2-ethanediyl(dimethyliminio)-1,3-propanediylimino-(1,6-dioxo-1,6-heptanediyl)imino-1,3-propanediyl-(dimethyliminio)-1,2-ethanediyl dichloride] | Luviquat 500 |
| 19 | Ethenol, polymer with aminomethyloxirane | Arlatone PQ-220 (ICI Americas) |
| 20 | Ethenyl octadecyl ether, polymer with aminomethyloxirane | Arlatone PQ-225 |
| 22 | Copolymer of Acrylic Acid and Diallyldimethylammonium Chloride | Merquat 280, 281, 280SD, 295 |
| 24 | Cellulose, 2-[2-Hydroxy-3-(Trimethyl-ammonio)Propoxy]Ethyl Ether, Chloride (Similar to PQ-10) | Quatrisoft Polymer LM-200 (Dow Chemical) |
| 27 | Hexanediamide, N,N'-bis(3-(Dimethyl-amino)Propyl)-, Polymer with N,N'-bis(3-Dimethylamino)Propyl Urea and 1,1'-Oxybis(2-Chloroethane), Block | |
| 28 | Copolymer of vinylpyrrolidone and methacrylamidopropyl trimethylammonium | Gafquat HS-100, Conditioneze NT-10 |
| 29 | Chitosan, 2,3-Dihydroxypropyl-2-Hydroxy-3-(Trimethylammonio)Propyl Ether, Chloride | Quaternized Chitosan |
| 30 | Ethanaminium, NCarboxymethyl)-N,N-Dimethyl-2-((2-Methyl-1-Oxo-2-Propenyl)Oxy)-, Inner Salt, Polymer with Methyl 2-Methyl-2-Propenoate | Mexomere PX (Chimex) |
| 31 | 2-Propenenitrile, Homopolymer, Hydrolyzed, Block, Reaction Products with N,N-Dimethyl-1,3-Propanediamine, Di-Et Sulfate-Quaternized | Hypan QT100 (Lipo) |
| 32 | Poly(acrylamide 2-methacryloxyethyl-trimethyl ammonium chloride) | Cosmedia CTC (Cognis GmbH) - PQ-32 + other, Salcare SC92 (Ciba Corp.) PQ-32 + other |
| 33 | Ethanaminium, N,N,N-Trimethyl-2-[1-Oxo-2-Propenyl)Oxy]-, Chloride, Polymer with 2-Propenamide | Lanoquat DES-50, Ultimer CG-200 (Nalco), Sepigel Quat33 (Seppic) - PQ-33 + other |
| 34 | Poly(diethyliminio-1,3-propanediyldi-methyliminio-1,3-propanediyl dibromide) | Mexomere PAK (Chimex) |
| 35 | Ethanaminium, N-carboxymethyl-N,N-dimethyl-2-(2-methyl-1-oxo-2-propenyloxy)-, inner salt, polymer with N,N,N-trimethyl-2-(2-methyl-1-oxo-2-propenyloxy)ethanaminium methyl sulfate | Plex 3074 L (Rohm GmbH) |
| 36 | 2-Propenoic Acid, 2-Methyl-,2-(Dimethylamino)Ethyl Ester, Polymer with Methyl 2-Methyl-2-Propenoate, compd. with Dimethyl Sulfate | Plex 4739L (Rohm GmbH) |
| 37 | N,N,N-Trimethyl-2-[(Methyl-1-Oxo-2-Propenyl)Oxy]Ethanaminium Chloride, | Ultragel 300 (Cognis), Synthalen CN, CR, CU (3V |

TABLE 2-continued

Deposition Aids - Cationic Polyquaternium Polymers

| Polyquaternium | Description | Commercial Products |
|---|---|---|
|  | Homopolymer | Group), Syntran PC 5320 (Interpolymer) |
| 39 | 2-Propen-1-aminium, N,NDimethyl-N-2-Propenyl-, Chloride, Polymer with 2-Propenamide and 2-Propenoic Acid | Merquat 3940, PLUS-3330, PLUS-3331, 3331PR |
| 42 | Poly[oxyethylene(dimethyliminio)ethylene (dimethylimino)ethylene dichloride] | Busan 1507 (Buckman Labs) |
| 43 | polymeric quaternary ammonium salt formed from acrylamide, acrylamidopropyltrimonium chloride, 2-amidopropylacrylamide sulfonate, and DMAPA monomers | Genamin PQ 43 (Clariant Functional Chemicals), Bozequat 4000 (Clariant) |
| 44 | Poly(2-oxopyrrolidin-1-ylethylene, 3-methylimidazolium-1-ylethylene methyl sulfate) | Luviquat Ultracare, MS 370 (BASF), Softenol PQ44 (Zdchimmer & Schwarz Italianat S.p.A) |
| 45 | Glycine, N-methyl-N-[2-[(2-methyl-1-oxo-2-propenyl)oxy]ethyl]-, polymer with 2-(dimethylamino)ethyl 2-methyl-2-propenoate, compound with dimethyl sulfate | Plex 3073L (Rohm GmbH) |
| 46 | 1H-Imidazolium, 1-Ethenyl-3-Methyl-, Methyl Sulfate, Polymer with 1-Ethenyl-hexahydro-2H-Azepin-2-one and 1-Ethenyl-2-Pyrrolildinone | Luviquat Hold |
| 47 | 1-Propanaminium, N,N,NTrimethyl-3-((2-Methyl-1-Oxo-2-Propenyl)Amino)-, Chloride, Polymer with Methyl 2-Propenoate and 2-Propenoic Acid | Merquat 2001, 2001N |
| 48 | Polymeric quaternary ammonium salt of formed from methacryloyl ethyl betaine, 2-hydroxyethyl methacrylate and methacryloyl ethyl trimethyl ammonium chloride | Plascize L-450 (Goo Chemical) |
| 49 | polymeric quaternary ammonium salt formed by the reaction of methacryloyl ethyl betaine, PEG-9 methacrylate and methacryloyl ethyl trimethyl ammonium chloride | Plascize L-440 (Goo Chemical) |
| 50 | Carboxylatoethyldimethylammonioethyl 2-methyl-2-propenoate homopolymer | Plascize L-401 (Goo Chemical) |
| 51 | 3,5,8-Triox-4-Phosphaundec-10-en-1-aminium, 4-Hydroxy-N,N,N,10-Tetramethyl-9-Oxo, Inner Salt, 4-Oxide, Polymer with Butyl 2-Methyl-2-Propenoate | Lipidure PMB (NOF) |
| 53 | Acrylic Acid/Acrylamide/Methacryl-amidopropyltrimonium Chloride Copolymer | Merquat 2003PR |
| 54 | Aspartic acid, polymer with C6-18 alkylamine, 3-dimethylaminopropylamine and sodium chloroacetate | Quilty-Hy (Mitsui) |
| 55 | 1-Dodecanaminium, N,NDimethyl-N-[3-[(2-Methyl-1-Oxo-2-Propenyl)-Amino-Propyl]-, Chloride, Polymer with N-[3-(Dimethylamino)Propyl]-2-Methyl-2-Propenamide and 1-Ethenyl-2-Pyrrolidinone | Styreze W |
| 56 | 5-Isocyanato-1-(isocyanatomethyl)-1,3,3-trimethylcyclohexane, polymer with 1,3-butanediol and bis(2-hydroxyethyl)di-methylammonium methyl sulfate | Hairrol UC-4 (Sanyo Chemical) |
| 57 | 12-Hydroxy-9(Z)-octadecenamidopropyl-trimethylammonium chloride, polymers with ricinus communis (castor) oil, isooctdecanoic acid and butandioic acid | Zenigloss Q (Zenitech) |
| 58 | 2-Propenoic Acid, Methyl Ester, Polymer with 2,2-Bis[(2-Propenyloxy)Methyl]-1-Butanol and Diethenylbenzene, Reaction Products with N,NDimethyl-1,3-Propane-diamine, Chloromethane-Quaternized | Lowenol Conditioner PWW (Lowenstein) - PQ-58 and Wheat Protein |
| 59 | Poly(20,25-dioxo-2,5,10,15,18-penta-methyl-10-(2-hydroxy-3-(3-phenyl-2-propenamido)propyldimethylammonio)-propyl)-10-azonia-1,4,7,13,16,19-hexaoxa-pentacosanediyl) chloride | Crodasorb UV-HPP (Croda, Inc.) - PQ-59 and Butylene Glycol |

TABLE 2-continued

Deposition Aids - Cationic Polyquaternium Polymers

| Polyquaternium | Description | Commercial Products |
|---|---|---|
| 60 | 9-Octadecenoic Acid, 12-Hydroxy-, [(2-Hydroxyethyl)-Imino]Di-2,1-Ethanediyl Ester, Polymer with 5-Isocyanato-1-(Isocyanatomethyl)-1,3,3-Trimethyl-cyclohexane, Compd. with Diethyl Sulfate | Polylipid PPI-RC (Alzo/Bernel) - PQ-60 and Propylene Glycol |
| 61 | 2-Methyl-2-propenoyloxyethyl N,N,N-trimethylammonioethyl phosphate inner salt, polymer with octadecyl 2-methyl-2-propenoate | Lipidure-S (NOF) |
| 62 | Polymeric quaternary ammonium salt of butyl methacrylate, polyethylene glycol methyl ether methacrylate, ethylene glycol dimethacrylate and 2-methacryloylethyl trimonium chloride with 2,2'-azobis(2-methyl propionamidine)dihydrochloride | Nanoaquasome (Amore Pacific/Kyung-do) |
| 63 | polymeric quaternary ammonium salt formed by acrylamide, acrylic acid and ethyltrimonium chloride acrylate | Finquat (Innospec), Octacare PQ63 (Innospec Edison, NJ), OF-308 (WSP Chemical & Technology) |
| 64 | 2-Methyl-2-propenoyloxyethyl N,N,N-trimethylammonioethyl phosphate inner salt, polymer with 2-hydroxy-3-(2-methyl-2-propenoyl)oxypropyltrimethyl-ammonium chloride | Lipidure-C (NOF) |
| 65 | 2-Methyl-2-propenoyloxyethyl N,N,N-trimethylammonioethyl phosphate inner salt, polymer with butyl 2-methyl-2-propenoate and sodium 2-methyl-2-propenoate | Lipidure-A (NOF) |
| 66 | 5-Isocyanato-1-(isocyanatomethyl)-1,3,3-trimethylcyclohexane, polymer with di(hydroxypolymethylene) benzene-dicarboxylate and ethylbis(2-hydroxy-ethyl)methylammonium ethyl sulfate | WBR-2925C (Taisei) - PQ-66 and Methyl Pyrrolidone |
| 67 | 2-Hydroxyethyl cellulose ether, reaction products with N,N,N-trimethyl-N-oxiranylmethylammonium chloride and N-dodecyl-N,N-dimethyl-N-oxiranylmethylammonium chloride | Softcat (Dow Chemical) |
| 68 | 1-Ethenyl-2-pyrrolidinone, polymer with 1-ethenylimidazole and 1-ethenyl-3-methylimidazolium methyl sulfate | Luviquat Supreme |
| 69 | polymeric quaternary ammonium salt composed of vinyl caprolactam, vinylpyrrolidone, dimethylaminopropyl methacrylamide (DMAPA), and methacryloylaminopropyl lauryldimonium chloride | Aquastyle 100, 300 (ISP) |
| 70 | polymeric quaternary ammonium salt consisting of an ethoxylated, propoxylated stearyl amine condensed with adipic acid and dilinoleic acid and quaternized with dimethyl sulfate | Lustreplex (Croda) |
| 71 | | ColaMoist 300P (Colonial Chemical Inc) |
| 72 | polymeric quaternary ammonium salt of hydroxethylcellulose reacted with a coco-alkyl dimethyl ammonium substituted epoxide | Mirustyle CP (Croda) |
| 73 | polymeric quaternary ammonium salt consisting of propyltrimonium chloride acrylamide, ethyltrimonium chloride methacrylate and dimethylacrylamide monomers; Propanaminium, N,N,N-trimethyl-3-(2-propenamido)-, chloride, polymer with N,N,N-trimethyl-2-(2-methyl-2-propenoyloxy)ethanaminium chloride and N,N-dimethyl-2-propenamide | Diaformer C-802, C-823 (Mitsubishi Chem), Diasleek C-802, C-823 (Mitsubishi Chem) |
| 74 | | Mirapol PB 20 (Rhodia) Polycare Boost (Rhodia) |
| 75 | O-(2-Hydroxy-2-trimethylammonio-propyl)starch chloride, reaction products with O-(3-dodecyldimethylammonio-2-hydroxypropyl)starch chloride | Amylomer Cat 220EMU (Grafe Chemie) |
| 76 | | Mirapol AT-1 (Rhodia) |

TABLE 2-continued

Deposition Aids - Cationic Polyquaternium Polymers

| Polyquaternium | Description | Commercial Products |
|---|---|---|
| 77 | Cocoglucoside Crosspolymer Hydroxypropyltrimonium Chloride | Colonial Poly SugaQuat TM-8610P (Colonial Chemical Inc) |
| 78 | Decylglucoside Crosspolymer Hydroxypropyl Laurdimonium Chloride | Colonial Poly SugaQuat L-1010P (Colonial Chemical Inc) |
| 79 | Decylglucoside Crosspolymer Hydroxypropyl Steardimonium Chloride | Colonial Poly SugaQuat S-1010P (Colonial Chemical Inc) |
| 80 | Laurylglucoside Crosspolymer Hydroxypropyl Laurdimonium Chloride | Colonial Poly SugaQuat L-1210P (Colonial Chemical Inc) |
| 81 | Laurylglucoside Crosspolymer Hydroxypropyl Steardimonium Chloride | Colonial Poly SugaQuat S-1210P (Colonial Chemical Inc) |
| 82 | Laurylglucoside Crosspolymer Hydroxypropyltrimonium Chloride | Colonial Poly SugaQuat TM-1218P (Colonial Chemical Inc) |
| 84 | polymeric quaternary ammonium salt of acrylamidopropyltrimethylammonium chloride, trimethylaminoethyl methacrylate, dimethylacrylamide and hydroxyethylmethacrylate | Diasleek C-824 (Mitsubishi Chemical) |
| 85 | polymeric quaternary ammonium salt of acrylamidopropyltrimethylammonium chloride, dimethylacrylamide and hydroxyethylmethacrylate | Diasleek C-825 (Mitsubishi Chemical) |
| 86 | polymeric quaternary ammonium salt of vinylpyrrolidone, 1-methyl-3-vinylimidazoline chloride, vinylimidazole and methacrylic acid | Luvigel Advanced (BASF) |
| 87 | polymeric quaternary ammonium salt of vinylpyrrolidone, vinylimidazole and diallyldimethyl ammonium chloride | Luviquat Sensation (BASF) |
| 88 | Poly(Dilinoleyldimonium hydroxypropyl)chlorides) | ColaQuat PDQ (Colonial Chemical Inc) |
| 89 | polymeric quaternary ammonium salt prepared by the reaction of t-butyl acrylate, vinyl pyrolidone, dimethylaminopropyl methacrylamide, methacrylic acid and ethyldimethyl[2-[(2-methyl-1-oxoallyl)oxy]ammonium ethyl sulfate, neutralized with orthophosphoric acid | (BASF) |
| 90 | polymeric quaternary ammonium salt of acrylamide and hydroxyethylcellulose quaternized with diallyldimethyl ammonium chloride | Hymoquat AK325R (Hymo Corporation) |
| 91 | polymeric quaternary ammonium salt of hydroxypropyl methacrylate and polyethylene glycol methacrylate quaternized with ethyltrimonium chloride methacrylate | Syntran 5500 (Interpolymer) - PQ-91 and PA |
| 92 | GLYCERYLAMIDOETHYL METHACRYLATE/STEARYL METHACRYLATE COPOLYMER | Ceracute-G (NOF) |
| 94 | polymeric quaternary ammonium salt consisting of acrylamide, dimethyl diallyl ammonium chloride and methacrylamidopropyltrimonium chloride monomers | (Toho) |
| 95 | copolymer of Zea Mays (Corn) Starch, Acrylic Acid and acrylamidopropyltrimethylammonium chloride monomers | Polyquart Ecoclean (Cognis) |
| 98 | | (Cognis GmbH) |
| 101 | | Deposilk Q1 (Air Products) |

Other suitable deposition aids include those described in US 2013/0330292, US 2013/0337023, US 2014/0017278.

Additional Components

The microcapsule composition of this invention can include one or more non-confined unencapsulated active materials from 0.01 to 50%, more preferably from 5 to 40%.

The microcapsule composition can also contain one or more other delivery system such as polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof. More exemplary delivery systems that can be incorporated are coascervate capsules, cyclodextrin delivery systems, and pro-perfumes.

(1) Melt extruded flavor/fragrance. Polymer assisted delivery system include melt extruded flavor/fragrance utilizing high molecular weight carbohydrates, low molecular weight carbohydrates, or polymer.

(1.1) High molecular weight carbohydrate including starches, modified starches.

(1.2) Low molecular weight carbohydrates of a low molecular weight carbohydrate or polyol, wherein said low molecular weight carbohydrate or polyol is selected from the group consisting of glucose, sucrose, maltose, lactose, corn syrup solid, erythritol, lactitol, mannitol, sorbitol, maltitol, isomalt, xylitol, trehalose, hydrogenated corn syrup, hydrogenated glucose syrup, hydrogenated maltose syrup, hydrogenated lactose syrup, starch hydrolysate, and a mixture thereof, and wherein said glassy matrix has a glass transition temperature of greater than room temperature.

(1.3) Polymers (various polymers are useful in the practice of our invention. Specific examples of polymers useful in the practice of our invention are as follows: DYLAN® of low density polyethylene (DYLAN® is a trademark owned by the Atlantic Richfield Company of Los Angeles, Calif.), DYLITE® of expandable polystyrene compositions (DYLITE® is a trademark of the Atlantic Richfield Company of Los Angeles, Calif.), and SUPER DYLAN® of high density polyethylene (SUPER DYLAN® is a trademark of the Atlantic Richfield Company of Los Angeles, Calif.)

Blended polyethylene and carbon black as specifically taught in U.S. Pat. No. 4,369,267 issued on Jan. 18, 1983, the specification for which is incorporated by reference herein.

Polystyrene as disclosed in U.S. Pat. No. 4,369,227 issued on Jan. 18, 1983, the specification for which is incorporated by reference herein. Polyene/alpha-olefin copolymers as exemplified and disclosed in U.S. Pat. No. 4,369,291, the specification for which is incorporated by reference herein. Poly-alpha-olefins as exemplified in Canadian Letters Pat. No. 1,137,069 issued on Dec. 7, 1982, the specification for which is incorporated by reference herein. Polymeric compositions as disclosed in Canadian Letters Pat. No. 1,137,068 issued on Dec. 7, 1982, the specification for which is incorporated by reference herein. Poly-alpha-olefins disclosed in Canadian Letters Pat. No. 1,137,067, the specification for which is incorporated by reference herein.

Polyolefins described in Canadian Letters Pat. No. 1,137,066, the specification for which is incorporated by reference herein. Polyethylene oxides as disclosed in Canadian Letters Pat. No. 1,137,065 issued on Dec. 7, 1982, the specification for which is incorporated by reference herein.

Olefin polymers and co-polymers as disclosed in Canadian Letters Pat. No. 1,139,737, the disclosure of which is incorporated by reference herein. Canadian Pat. No. 1,139,737 was issued on Jan. 18, 1983. Polyolefins disclosed in Canadian Letters Pat. No. 1,139,738, the specification for which is incorporated by reference herein. Canadian Pat. No. 1,139,738 was issued on Jan. 18, 1983. Chlorinated PVC as disclosed in Polymer 1982, 23 (7, Suppl.), 1051-6 abstracted at Chem. Abstracts 97:145570y, 1982.

Polyepsilon caprolactone co-polymers made by means of alcohol initiated polymerization as disclosed in J. Polym. Sci. Polym. Chem. Ed. 1982, 20(2), pages 319-26, abstracted at Chem. Abstracts, Volume 96: 123625x, 1982. Styrene acrylonitrile co-polymers as disclosed in Diss. Abstracts, Int. B, 1982, 42(8), 3346 and abstracted at Chem. Abstracts 96:143750n (1982). Co-polymers of epsilon caprolactone with 1,4-butane diol as disclosed at Kauch. Rezine, 1982, (2), 8-9, abstracted at Chem. Abstracts, volume 96:182506g (1982). Polyesters as disclosed in U.S. Pat. No. 4,326,010, the specification for which is incorporated by reference herein.

Chlorinated polyethylene as disclosed by Belorgey, et. al. J. Polym. Sci. Polym. Phys. Ed. 1982, 20(2), 191-203. Plasticized polyepsilon caprolactone co-polymers containing dimethyl phthalate plasticizers as set forth in Japanese Pat. No. J81/147844, abstracted at Chem. Abstracts, Volume 96:69984y (1982), the specification for which is incorporated by reference herein. Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein. Polyurethane polymers having lactone backbones as disclosed in U.S. Pat. No. 4,156,067 issued on May 22, 1979, the disclosure of which is incorporated by reference herein. Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein. Resins having polyurethane backbones as disclosed in U.S. Pat. No. 3,975,350 issued on Aug. 17, 1976, the disclosure of which is incorporated by reference herein.

(1.4) Suitable plasticizers include water; glycerol; propylene glycol; aqueous solutions of glycerol, propylene glycol, monosaccharides, and disaccharides; and invert and high fructose corn syrups.

(1.5) Emulsifier. surface-active agent, i.e. an emulsifier can be added to the dry blend, or preferably added to the liquid flavor mix which is ultimately injected into the metering zone of the extruder. These emulsifiers can be from the class of distilled monoglycerides, mono- and diglyceride blends, propyleneglycol monoglycerides, lecithin, modified lecithins, acetylated monoglycerides, lactylated monoglycerides, lactylated propyleneglycol monoglycerides, sorbitan esters, sorbitan-polyoxyethylene [20] monoglycerides, polyglycerol esters, DATEM's (diacetyltartarate esters of monoglycerides), succinylated esters of monoglycerides and polyoxyethylenepropylene copolymers and mixtures thereof. Most preferred surfactants are the sorbitan-polyoxyethylene [20] monoglycerides, lecithins, and polyglycerol esters.

(2) Spray Dry Encapsulation.

(2.1) The matrix is comprised of one or more of the following materials: sugars such as glucose, fructose, lactose, galactose, ribose, xylose, sucrose, maltose; polyols such as glycerin and propylene glycol; corn syrups, maltodextrin, fats, silicone dioxide, polyhydric alcohols, corn syrup solids, starches, modified starches, emulsifiers and food acids. The level of maltodextrin used in the matrix, comprises from 25 to 98 weight percent, preferably form 35 to 75 weight percent, the maltodextrin (2.2) Core modifiers: flavors and fragrance may also be combined with a variety of solvents which serve to increase the compatibility of the various materials, increase the overall hydrophobicity of the blend, influence the vapor pressure of the materials, or serve to structure the blend. Solvents performing these functions are well known in the art and include mineral oils, triglyceride oils, silicone oils, fats, waxes, fatty alcohols, diisodecyl adipate, and diethyl phthalate among others.

(2.3) emulsifiers including monoglycerides of fatty acids, distilled succinylated monoglycerides of fatty acids, sorbitan fatty acid esters; distilled acetylated monoglycerides of fatty acids, monoglycerides of fatty acids.

(3) Coascervate Capsules.

(3.1) Proteins useful in coacervation processes include albumins, vegetable globulins and gelatines. The gelatine may be fish, pork, beef, and/or poultry gelatine, for example. According to a preferred embodiment, the protein is fish, beef or poultry gelatine. According to a more preferred embodiment, the protein is warm water fish gelatine.

(3.2) Typical non-protein polymers useful in complex coacervation methods include, in particular, negatively charged polymers. For example, they may be selected from gum arabic, xanthan, agar, alginate salts, cellulose derivatives, for example carboxymethyl cellulose, pectinate salts, carrageenan, polyacrylic and methacrylic acid, and/or mixtures thereof. Further suitable non-proteins can be derived from the literature, for example from to WO 2004/022221, page 4, lines 27-29

(3.3) A cross-linking agent is typically used to harden the coating layer. Suitable cross-linking agents include formaldehyde, acetaldehyde, glutaraldehyde, glyoxal, chrome alum, or transglutaminase. Preferably, transglutaminase is used at 10-100, preferably 30-60 activity units per gram of gelatine. This enzyme is well described and commercially obtainable.

(4) Cyclodextrin Delivery System

This technology approach uses a cyclic oligosaccharide or cyclodextrin to improve the delivery of perfume. Typically, a perfume and cyclodextrin (CD) complex is formed. Such complexes may be pre-formed, formed in-situ, or formed on or in the situs. See, e.g., WO 2013/109798 A2 and US 2011/0308556 A1.

(5) Pro-Perfume (5.1) Michael Addition reaction products of a primary/secondary amine with an unsaturated ester, acid or nitrile perfume compound such those described in U.S. Pat. No. 6,858,575.

(5.2) Reaction product between a primary/secondary amine compound/polymer and a ketone or aldehyde perfume compound such as those described in WO 2001/051599 A1 and WO 2002/092746 A1

(5.3) other nonlimiting examples include aromatic or non-aromatic imines (Schiff bases), oxazolidines, beta-keto esters, orthoesters, compounds comprising one or more beta-oxy or beta-thio carbonyl moieties capable of releasing a perfume (e.g., an alpha, beta-unsaturated ketone, aldehyde or carboxylic ester). The typical trigger for perfume release is exposure to water; although other triggers may include enzymes, heat, light, pH change, autoxidation, a shift of equilibrium, change in concentration or ionic strength and others. Suitable pro-perfumes and methods of making same can be found in U.S. Pat. Nos. 8,912,350 B2, 7,018,978 B2; 6,987,084 B2; 6,956,013 B2; 6,861,402 B1; 6,544,945 B1; 6,093,691; 6,277,796 B1; 6,165,953; 6,316,397 B1; 6,437,150 B1; 6,479,682 B1; 6,096,918; 6,218,355 B1; 6,133,228; 6,147,037; 7,109,153 B2; 7,071,151 B2; 6,987,084 B2; 6,916,769 B2; 6,610,646 B2 and 5,958,870, as well as can be found in US 2005/0003980 A1 and US 2006/0223726 A1.

Any compound, polymer, or agent discussed above can be the compound, polymer, or agent itself as shown above, or its salt, precursor, hydrate, or solvate. A salt can be formed between an anion and a positively charged group on the compound, polymer, or agent. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group on the compound, polymer, or agent. Suitable cations include sodium ion, potassium ion, magnesium ion, calcium ion, and an ammonium cation (e.g., tetramethylammonium ion). A precursor can be ester and another suitable derivative, which, during the process of preparing a polyurea or polyurethane capsule composition of this invention, is capable of converting to the compound, polymer, or agent and being used in preparing the polyurea or polyurethane capsule composition. A hydrate refers to the compound, polymer, or agent that contains water. A solvate refers to a complex formed between the compound, polymer, or agent and a suitable solvent. A suitable solvent can be water, ethanol, isopropanol, ethyl acetate, acetic acid, and ethanolamine.

Certain compounds, polymers, and agents have one or more stereocenters, each of which can be in the R configuration, the S configuration, or a mixture. Further, some compounds, polymers, and agents possess one or more double bonds wherein each double bond exists in the E (trans) or Z (cis) configuration, or combinations thereof. The compounds, polymers, and agents include all possible configurational stereoisomeric, regioisomeric, diastereomeric, enantiomeric, and epimeric forms as well as any mixtures thereof. As such, lysine used herein includes L-lysine, D-lysine, L-lysine monohydrochloride, D-lysine monohydrochloride, lysine carbonate, and so on. Similarly, arginine includes L-arginine, D-arginine, L-arginine monohydrochloride, D-arginine monohydrochloride, arginine carbonate, arginine monohydrate, and etc. Guanidine includes guanidine hydrochloride, guanidine carbonate, guanidine thiocyanate, and other guanidine salts including their hydrates. Ornithine include L-ornithine and its salts/hydrates (e.g., monohydrochloride) and D-ornithine and its salts/hydrates (e.g., monohydrochloride).

The microcapsule composition of this invention can be a slurry containing in a solvent (e.g., water) the capsule at a level of 0.1 to 80% (preferably 1 to 65% and more preferably 5 to 45%) by weight of the capsule delivery system.

In some embodiments, the microcapsule composition slurry is purified by washing the capsule slurry with water, e.g., deionized or double deionized water, until a neutral pH is achieved. For the purposes of the present invention, the capsule suspension can be washed using any conventional method including the use of a separatory funnel, filter paper, centrifugation and the like. The capsule suspension can be washed one, two, three, four, five, six, or more times until a neutral pH, e.g., pH 6-8 and 6.5-7.5, is achieved. The pH of the purified capsules can be determined using any conventional method including, but not limited to pH paper, pH indicators, or a pH meter.

A capsule suspension of this invention is "purified" in that it is 80%, 90%, 95%, 97%, 98% or 99% homogeneous to capsules. In accordance with the present invention, purity is achieved by washing the capsules until a neutral pH is achieved, which is indicative of removal of unwanted impurities and/or starting materials, e.g., polyisocyanate, cross-linking agent and the like.

In certain embodiments of this invention, the purification of the capsules includes the additional step of adding a salt to the capsule suspension prior to the step of washing the capsule suspension with water. Exemplary salts of use in this step of the invention include, but are not limited to, sodium chloride, potassium chloride or bi-sulphite salts. See US 2014/0017287.

The microcapsule composition of this invention can also be spray dried to a solid form. In a spray drying process, a spray dry carrier is added to a microcapsule composition to assist the removal of water from the slurry.

According to one embodiment, the spray dry carriers can be selected from the group consisting of carbohydrates such as chemically modified starches and/or hydrolyzed starches, gums such as gum arabic, proteins such as whey protein, cellulose derivatives, clays, synthetic water-soluble polymers and/or copolymers such as polyvinyl pyrrolidone, polyvinyl alcohol. The spray dry carriers may be present in an amount from 1 to 50%, more preferably from 5 to 20%.

Optionally, a free flow agent (anticaking agent) of silicas which may be hydrophobic (i.e. silanol surface treated with halogen silanes, alkoxysilanes, silazanes, siloxanes, etc.

such as Sipernat D17, Aerosil R972 and R974 (available from Degussa), etc.) and/or hydrophilic such as Aerosil 200, Sipernat 22S, Sipernat 50S, (available from Degussa), Syloid 244 (available from Grace Davison), may be present from 0.01 to 10%, more preferable from 0.5 to 5%.

Humectants and viscosity control/suspending agents can also be added to facilitate spray drying. These agents are disclosed in U.S. Pat. Nos. 4,428,869, 4,464,271, 4,446,032, and 6,930,078. Details of hydrophobic silicas as a functional delivery vehicle of active materials other than a free flow/anticaking agent are disclosed in U.S. Pat. Nos. 5,500,223 and 6,608,017.

The spray drying inlet temperature is in the range of 150 to 240° C., preferably between 170 and 230° C., more preferably between 190 and 220° C.

As described herein, the spray-dried microcapsule composition is well suited for use in a variety of all dry (anhydrous) products: powder laundry detergent, fabric softener dryer sheets, household cleaning dry wipes, powder dish detergent, floor cleaning cloths, or any dry form of personal care products (e.g. shampoo powder, deodorant powder, foot powder, soap powder, baby powder), etc. Because of high fragrance and/or active agent concentration in the spray-dried products of the present invention, characteristics of the aforementioned consumer dry products will not be adversely affected by a small dosage of the spray-dried products.

The microcapsule composition can also be sprayed as a slurry onto a consumer product, e.g., a fabric care product. By way of illustration, a liquid delivery system containing capsules is sprayed onto a detergent powder during blending to make granules. See US 2011/0190191. In order to increase fragrance load, water-absorbing material, such as zeolite, can be added to the delivery system.

Alternatively, granulates in a consumer product are prepared in a mechanical granulator in the presence of a granulation auxiliary such as non-acid water-soluble organic crystalline solids. See WO 2005/097962.

Zeta Potentials and Rupture Forces

The first microcapsule of this invention is positively charged as indicated by a zeta potential of at least 10 mV, preferably at least 25 mV (e.g., 25 to 200 mV), and more preferably at least 40 mV (e.g., 40 to 100 mV). The second microcapsule is either neutral (having a zeta potential of 5 to −5 mV) or negatively charged (having a zeta potential of −10 mV or less).

Zeta potential is a measurement of electrokinetic potential in the microcapsule slurry. From a theoretical viewpoint, zeta potential is the potential difference between the water phase (i.e., the dispersion medium) and the stationary layer of water attached to the surface of the microcapsule.

The zeta potential is a key indicator of the stability of the microcapsule in the microcapsule compositions or in consumer products. Typically, a microcapsule having a zeta potential of 10 to 25 mV shows a moderate stability. Similarly, a microcapsule having a zeta potential of 25 to 40 mV shows a good stability and a microcapsule having a zeta potential of 40 to 100 mV shows excellent stability. Not to be bound by any theory, the microcapsule of this invention has a desirable zeta potential making it suitable for use in consumer products with improved stability.

Zeta potential is calculated using theoretical models and an experimentally-determined electrophoretic mobility or dynamic electrophoretic mobility. For more detailed discussion on measurement of zeta potential, see Dukhin, A. S. and Goetz, P. J. "Ultrasound for characterizing colloids", Elsevier, 2002.

The first and second microcapsules of this invention each independently can have a fracture strength of 0.2 to 80 MPa (e.g., 0.5 to 60 MPa, 1 to 50 MPa, and 5 to 30 MPa). The fracture strength of each microcapsule is calculated by dividing the rupture force (in Newtons) by the cross-sectional area of the respective microcapsule ($\pi r2$, where r is the radius of the particle before compression). The measurement of the rupture force and the cross-sectional area is performed following the methods described in Zhang et al., *J Microencapsulation* 18(5), 593-602 (2001).

The first and second microcapsules each can have a rupture force of less than 10 mN (e.g., 0.1 to 10 mN, 0.2 to 8 mN, 0.3 to 5 mN, and 0.1 to 2 mN). The rupture force is the force needed to rupture the microcapsules. Its measurement is based on a technique known in the art as micromanipulation. See Zhang et al., *Journal of Microencapsulation* 16(1), 117-124 (1999).

Hair Care Products

The microcapsule composition of this invention is especially suitable for use in hair care products including hair conditioning products.

Hair conditioner products includes hair conditioners, leave-on hair conditioner, leave-in conditioner, rejuvenating conditioner, creme rinse, oil-free hair conditioners, rinse-off hair conditioner, conditioning rinse, foaming conditioner, conditioning styling gel, conditioning mousse, spay-on conditioner, hair dressing creme and hair repair spray.

The term "leave-on" refers to a hair care composition that is applied to the hair and not further subjected to a rinsing step. The term "rinse-out" as contrasted with the term "leave on" is used herein to mean compositions which are used in a context whereby the composition is ultimately rinsed or washed from the hair either after or during the application of the product.

Conditioning agents include any material which is used to give a particular conditioning benefit to hair. Suitable conditioning agents are those which deliver one or more benefits relating to shine, softness, comb ability, antistatic properties, wet-handling, damage, manageability, body, and greasiness. Examples include silicones (e.g. silicone oils, cationic silicones, silicone gums, high refractive silicones, silicone quaternary compounds, and silicone resins), organic conditioning oils (e.g., hydrocarbon oils, polyolefins, fatty acids, fatty alcohols, and fatty esters), alkyl quaternaries, and combinations thereof. See U.S. Pat. No. 6,696,053 and WO 2017/127494.

The concentration of the conditioning agent in the hair conditioner products should be sufficient to provide the desired conditioning benefits, and as will be apparent to one of ordinary skill in the art (e.g., 0.1 to 30%, 0.1 to 20%, 0.1 to 10%, and 0.1 to 6%).

The microcapsule composition can be present at a level of 0.02 to 15% (e.g., 0.05 to 10%, 0.1 to 5%, and 0.5 to 3%) so that the hair conditioning composition has a fragrance load of 0.01 to 5% (e.g., 0.02 to 3%, 0.05 to 2%, and 0.1 to 1%). The term "fragrance load" refers to the percentage of the fragrance by weight of the consumer product, e.g., the hair conditioning composition.

The hair care products of this invention contain any one of the microcapsule described above and a conditioning agent. Optional additional components that can be included in the hair care products are cationic thickeners, carriers, emollients, moisturizing agents, hair soothing agents, antioxidants/radical scavengers, chelators or chelating agents, anti-inflammatory agents antimicrobial actives, sunscreen actives, antidandruff agents, styling agents, hair bodying and volumizing agents, and combinations thereof. See U.S. Pat. No. 6,696,053 and WO 2017/127494.

Fabric Conditioning Products

The microcapsule composition of this invention is also suitable for use in fabric care products such as fabric conditioning products.

The fabric conditioning compositions having the microcapsule composition contains at least one fabric conditioning agent, preferably at a concentration of 1 to 30% (e.g., 4 to 20%, 4 to 10%, and 8 to 15%). It would be obvious to a skilled person in the art to determine the concentration of a fabric conditioning agent while keeping its conditioning benefits and also maintaining a reasonable stability and shelf life.

Suitable fabric conditioning agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390. Suitable softening agents include esterquats such as Rewoquat WE 18 commercially available from Evonik Industries and Stepantex SP-90 commercially available from Stepan Company.

The microcapsule composition can be present at a level of 0.02 to 15% (e.g., 0.05 to 10%, 0.1 to 5%, and 0.5 to 3%) so that the fabric conditioning composition has a fragrance load of 0.01 to 5% (e.g., 0.02 to 3%, 0.05 to 2%, and 0.1 to 1%).

Applications.

The microcapsule composition of the present invention are well-suited for use, without limitation, in the following products:

a) Household products
i. Liquid or Powder Laundry Detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818
ii. Unit Dose Pouches, Tablets and Capsules such as those described in EP 1 431 382 A1, US 2013/0219996 A1, US 2013/0284637 A1, and U.S. Pat. No. 6,492,315. These unit dose formulations can contain high concentrations of a functional material (e.g., 5-100% fabric softening agent or detergent active), fragrance (e.g., 0.5-100%, 0.5-40%, and 0.5-15%), and flavor (e.g., 0.1-100%, 0.1-40%, and 1-20%). They can contain no water to limit the water content as low as less than 30% (e.g., less than 20%, less than 10%, and less than 5%).
iii. Scent Boosters such as those described in U.S. Pat. Nos. 7,867,968, 7,871,976, 8,333,289, US 2007/0269651 A1, and US2014/0107010 A1.
iv. Fabric Care Products such as Rinse Conditioners (containing 1 to 30 weight % of a fabric conditioning active), Fabric Liquid Conditioners (containing 1 to 30 weight % of a fabric conditioning active), Tumble Drier Sheets, Fabric Refreshers, Fabric Refresher Sprays, Ironing Liquids, and Fabric Softener Systems such as those described in U.S. Pat. Nos. 6,335,315, 5,674,832, 5,759,990, 5,877,145, 5,574,179, 5,562,849, 5,545,350, 5,545,340, 5,411,671, 5,403,499, 5,288,417, 4,767,547 and 4,424,134

Liquid fabric softeners/fresheners contains at least one fabric softening agent present, preferably at a concentration of 1 to 30% (e.g., 4 to 20%, 4 to 10%, and 8 to 15%). The ratio between the active material and the fabric softening agent can be 1:500 to 1:2 (e.g., 1:250 to 1:4 and 1:100 to 1:8). As an illustration, when the fabric softening agent is 5% by weight of the fabric softener, the active material is 0.01 to 2.5%, preferably 0.02 to 1.25% and more preferably 0.1 to 0.63%. As another example, when the fabric softening agent is 20% by weight of the fabric softener, the active material is 0.04 to 10%, preferably 0.08 to 5% and more preferably 0.4 to 2.5%. The active material is a fragrance, malodor counteractant or mixture thereof. The liquid fabric softener can have 0.15 to 15% of capsules (e.g., 0.5 to 10%, 0.7 to 5%, and 1 to 3%). When including capsules at these levels, the neat oil equivalent (NOE) in the softener is 0.05 to 5% (e.g., 0.15 to 3.2%, 0.25 to 2%, and 0.3 to 1%).

Suitable fabric softening agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390. Suitable softening agents include esterquats such as Rewoquat WE 18 commercially available from Evonik Industries and Stepantex SP-90 commercially available from Stepan Company.

v. Liquid dish detergents such as those described in U.S. Pat. Nos. 6,069,122 and 5,990,065
vi. Automatic Dish Detergents such as those described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562
vii. All-purpose Cleaners including bucket dilutable cleaners and toilet cleaners
viii. Bathroom Cleaners
ix. Bath Tissue
x. Rug Deodorizers
xi. Candles
xii. Room Deodorizers
xiii. Floor Cleaners
xiv. Disinfectants
xv. Window Cleaners
xvi. Garbage bags/trash can liners
xvii. Air Fresheners including room deodorizer and car deodorizer, scented candles, sprays, scented oil air freshener, Automatic spray air freshener, and neutralizing gel beads
xviii. Moisture absorber
xix. Household Devices such as paper towels and disposable Wipes
xx. Moth balls/traps/cakes b) Baby Care Products
  i. Diaper Rash Cream/Balm
  ii. Baby Powder
c) Baby Care Devices
  i. Diapers
  ii. Bibs
  iii. Wipes
d) Oral Care Products. Tooth care products (as an example of preparations according to the invention used for oral care) generally include an abrasive system (abrasive or polishing agent), for example silicic acids, calcium carbonates, calcium phosphates, aluminum oxides and/or hydroxylapatites, surface-active substances, for example sodium lauryl sulfate, sodium lauryl sarcosinate and/or cocamidopropylbetaine, humectants, for example glycerol and/or sorbitol, thickening agents, for example carboxymethyl cellulose, polyethylene glycols, carrageenan and/or Laponite®, sweeteners, for example saccharin, taste correctors for unpleasant taste sensations, taste correctors for further, normally not unpleasant taste sensations, taste-modulating substances (for example inositol phosphate, nucleotides such as guanosine monophosphate, adenosine monophosphate or other substances such as sodium glutamate or 2-phenoxypropionic acid), cooling active ingredients, for example menthol derivatives, (for example L-menthyllactate, L-menthylalkylcarbonates, menthone ketals, menthane carboxylic acid amides), 2,2,2-trialkylacetic acid amides (for example 2,2-diisopropylpropionic acid methyl amide), icilin and icilin derivatives, stabilizers and active ingredients, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings and/or sodium bicarbonate or taste correctors.
  i. Tooth Paste. An exemplary formulation as follows:
    1. calcium phosphate 40-55%
    2. carboxymethyl cellulose 0.8-1.2%
    3. sodium lauryl sulfate 1.5-2.5%
    4. glycerol 20-30%
    5. saccharin 0.1-0.3%
    6. flavor oil 1.0-2.5%
    7. water q.s. to 100%
      A typical procedure for preparing the formulation includes the steps of (i) mixing by a blender according to the foregoing formulation to provide a toothpaste, and (ii) adding a composition of this invention and blending the resultant mixture till homogeneous.
  ii. Tooth Powder
  iii. Oral Rinse
  iv. Tooth Whiteners
  v. Denture Adhesive
e) Health Care Devices
  i. Dental Floss
  ii. Toothbrushes
  iii. Respirators
  iv. Scented/flavored condoms
f) Feminine Hygiene Products such as Tampons, Feminine Napkins and Wipes, and Pantiliners
g) Personal Care Products: Cosmetic or pharmaceutical preparations, e.g., a "water-in-oil" (W/O) type emulsion, an "oil-in-water" (O/W) type emulsion or as multiple emulsions, for example of the water-in-oil-in-water (W/O/W) type, as a PIT emulsion, a Pickering emulsion, a micro-emulsion or nano-emulsion; and emulsions which are particularly preferred are of the "oil-in-water" (O/W) type or water-in-oil-in-water (W/O/W) type. More specifically,
  i. Personal Cleansers (bar soaps, body washes, and shower gels)
  ii. In-shower conditioner
  iii. Sunscreen ant tattoo color protection (sprays, lotions, and sticks)
  iv. Insect repellants
  v. Hand Sanitizer
  vi. Antiinflammatory balms, ointments, and sprays
  vii. Antibacterial ointments and creams
  viii. Sensates
  ix. Deodorants and Antiperspirants including aerosol and pump spray antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant, gel deodorant, spray deodorant, roll-on, and cream deodorant.
  x. Wax-based Deodorant. An exemplary formulation as follows:
    1. Paraffin Wax 10-20%
    2. Hydrocarbon Wax 5-10%
    3. White Petrolatum 10-15%
    4. Acetylated Lanolin Alcohol 2-4%
    5. Diisopropyl Adipate 4-8%
    6. Mineral Oil 40-60%
    7. Preservative (as needed)
      The formulation is prepared by (i) mixing the above ingredients, (ii) heating the resultant composition to 75° C. until melted, (iii) with stirring, adding 4% cryogenically ground polymer containing a fragrance while maintaining the temperature 75° C., and (iv) stirring the resulting mixture in order to ensure a uniform suspension while a composition of this invention is added to the formulation.
  xi. Glycol/Soap Type Deodorant. An exemplary formulation as follows:
    1. Propylene Glycol 60-70%
    2. Sodium Stearate 5-10%
    3. Distilled Water 20-30%
    4. 2,4,4-Trichloro-2'-Hydroxy Diphenyl Ether, manufactured by the Ciba-Geigy Chemical Company and a Trademark of the Ciba-Geigy Chemical Company) 0.01-0.5%
      The ingredients are combined and heated to 75° C. with stirring until the sodium stearate has dissolved. The resulting mixture is cooled to 40° C. followed by addition of a composition of this invention.
  xii. Lotion including body lotion, facial lotion, and hand lotion
  xiii. Body powder and foot powder
  xiv. Toiletries
  xv. Body Spray
  xvi. Shave cream and male grooming products
  xvii. Bath Soak
  xviii. Exfoliating Scrub h) Personal Care Devices
   i. Facial Tissues
   ii. Cleansing wipes
i) Hair Care Products
   i. Shampoos (liquid and dry powder)
   ii. Hair Conditioners (Rinse-out conditioners, leave-in conditioners, and cleansing conditioners)
   iii. Hair Rinses
   iv. Hair Refreshers
   v. Hair perfumes
   vi. Hair straightening products
   vii. Hair styling products, Hair Fixative and styling aids
   viii. Hair combing creams
   ix. Hair wax
   x. Hair foam, hair gel, nonaerosol pump spray
   xi. Hair Bleaches, Dyes and Colorants
   xii. Perming agents
   xiii. Hair wipes
j) Beauty Care
   i. Fine Fragrance—Alcoholic. Compositions and methods for incorporating fragrance capsules into alcoholic fine fragrances are described in U.S. Pat. No. 4,428,869. Alcoholic fine fragrances may contain the following:
      1. Ethanol (1-99%)
      2. Water (0-99%)
      3. A suspending aide including but not limited to: hydroxypropyl cellulose, ethyl cellulose, silica, microcrystalline cellulose, carrageenan, propylene glycol alginate, methyl cellulose, sodium carboxymethyl cellulose or xanthan gum (0.1-1%)
      4. Optionally an emulsifier or an emollient may be included including but not limited to those listed above
   ii. Solid Perfume
   iii. Lipstick/lip balm
   iv. Make-up cleanser
   v. Skin care cosmetic such as foundation, pack, sunscreen, skin lotion, milky lotion, skin cream, emollients, skin whitening
   vi. Make-up cosmetic including manicure, mascara, eyeliner, eye shadow, liquid foundation, powder foundation, lipstick and cheek rouge
k) Consumer goods packaging such as fragranced cartons, fragranced plastic bottles/boxes
l) Pet care products
   i. Cat litter
   ii. Flea and tick treatment products
   iii. Pet grooming products
   iv. Pet shampoos
   v. Pet toys, treats, and chewables
   vi. Pet training pads
   vii. Pet carriers and crates
m) Confectionaries confectionery, preferably selected from the group consisting of chocolate, chocolate bar products, other products in bar form, fruit gums, hard and soft caramels and chewing gum
   i. Gum
      1. Gum base (natural latex chicle gum, most current chewing gum bases also presently include elastomers, such as polyvinylacetate (PVA), polyethylene, (low or medium molecular weight) polyisobutene (PIB), polybutadiene, isobutene-isoprene copolymers (butyl rubber), polyvinylethylether (PVE), polyvinylbutyether, copolymers of vinyl esters and vinyl ethers, styrene-butadiene copolymers (styrene-butadiene rubber, SBR), or vinyl elastomers, for example based on vinylacetate/vinyllaurate, vinylacetate/vinylstearate or ethylene/vinylacetate, as well as mixtures of the mentioned elastomers, as described for example in EP 0 242 325, U.S. Pat. Nos. 4,518,615, 5,093,136, 5,266,336, 5,601,858 or U.S. Pat. No. 6,986,709.) 20-25%
      2. Powdered sugar 45-50%
      3. glucose 15-17%
      4. starch syrup 10-13%
      5. plasticizer 0.1%
      6. flavor 0.8-1.2%
         The components described above were kneaded by a kneader according to the foregoing formulation to provide a chewing gum. Encapsulated Flavor or sensate is then added and blended till homogeneous.
   ii. Breath Fresheners
   iii. Orally Dissolvable Strips
   iv. Chewable Candy
   v. Hard Candy
n) Baked products, preferably selected from the group consisting of bread, dry biscuits, cakes and other cookies;
o) snack foods, preferably selected from the group consisting of baked or fried potato chips or potato dough products, bread dough products and corn or peanut-based extrudates;
   i. Potato, tortilla, vegetable or multigrain chips
   ii. Popcorn
   iii. Pretzels
   iv. Extruded stacks
p) Cereal Products preferably selected from the group consisting of breakfast cereals, muesli bars and precooked finished rice products
q) Alcoholic and non-alcoholic beverages, preferably selected from the group consisting of coffee, tea, wine, beverages containing wine, beer, beverages containing beer, liqueurs, schnapps, brandies, sodas containing fruit, isotonic beverages, soft drinks, nectars, fruit and vegetable juices and fruit or vegetable preparations; instant beverages, preferably selected from the group consisting of instant cocoa beverages, instant tea beverages and instant coffee beverages
   i. Ready to drink liquid drinks
   ii. Liquid Drink Concentrates
   iii. Powder Drinks
   iv. Coffee: Instant Cappucino
      1. Sugar 30-40%
      2. Milk Powder 24-35%
      3. Soluble Coffee 20-25%
      4. Lactose 1-15%
      5. Food Grade Emulsifier 1-3%
      6. Encapsulated Volatile Flavor 0.01-0.5%
   v. Tea
   vi. Alcoholic
r) Spice blends and consumer prepared foods
   i. Powder gravy, sauce mixes
   ii. Condiments
   iii. Fermented Products
s) Ready to heat foods: ready meals and soups, preferably selected from the group consisting of powdered soups, instant soups, precooked soups
   i. Soups
   ii. Sauces
   iii. Stews
   iv. Frozen entrees t) Dairy Products milk products, preferably selected from the group consisting of milk beverages, ice milk, yogurt, kefir, cream cheese, soft cheese, hard cheese, powdered milk, whey, butter, buttermilk and partially or fully hydrolyzed milk protein-containing products Flavored milk beverages
  i. Yoghurt
  ii. Ice cream
  iii. Bean Curd
  iv. Cheese
u) Soya protein or other soybean fractions, preferably selected from the group consisting of soya milk and products produced therefrom, soya lecithin-containing preparations, fermented products such as tofu or tempeh or products produced therefrom and soy sauces;
v) Meat products, preferably selected from the group consisting of ham, fresh or raw sausage preparations, and seasoned or marinated fresh or salt meat products
w) Eggs or egg products, preferably selected from the group consisting of dried egg, egg white and egg yolk
x) Oil-based products or emulsions thereof, preferably selected from the group consisting of mayonnaise, remoulade, dressings and seasoning preparations
y) fruit preparations, preferably selected from the group consisting of jams, sorbets, fruit sauces and fruit fillings; vegetable preparations, preferably selected from the group consisting of ketchup, sauces, dried vegetables, deep-frozen vegetables, precooked vegetables, vegetables in vinegar and preserved vegetables
z) Flavored pet foods.

The above-listed applications are all well known in the art. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, and 4,767,547, 4,424,134. Liquid laundry detergents include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Liquid dish detergents are described in U.S. Pat. Nos. 6,069,122 and 5,990,065. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. Automatic Dish Detergents are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The terms "capsule" and "microcapsule" herein are used interchangeably.

The terms "polyfunctional isocyanate," "multifunctional isocyanate," and "polyisocyanate" all refer to a compound having two or more isocyanate (—NCO) groups.

The terms "polyfunctional amine," "multifunctional amine," and "polyamine" refers to a compound containing one, two or more primary or secondary amine groups. These terms also refers to a compound containing one or more primary/secondary amine groups and one or more hydroxyl groups (—OH).

The terms "polyethyleneimine," "polyethyleneimines," "polyethylenimine," and "polyethylenimines" are used interchangeably.

The terms "polyfunctional alcohol," "multifunctional alcohol," "poly alcohol," and "polyol" refer to a compound having two or more hydroxyl groups.

The term "degree of polymerization" refers to the number of repeat units in a polymer.

The term "degree of crosslinking" refers to percent of interconnecting units over the total repeat unit. It is generally measured by swelling experiments. See ASTM Standard Test Method ASTM D2765-11; Lange, Colloid & Polymer Science 264, 488-93 (1986).

The terms "multi-functional nucleophile" and "polyfunctional nucleophile" are used herein interchangeably. They both refer to an aliphatic or aromatic hydrocarbon onto which is attached two or more nucleophilic groups such as primary/secondary amine groups and the hydroxyl group.

The term "multi-functional electrophile" and "polyfunctional electrophile" are used interchangeably and refer to an aliphatic or aromatic hydrocarbon, onto which is attached two or more electrophilic groups reactive towards the nucleophilic group. Examples of an electrophilic group include: aldehydes, halide, sulfate esters, sulphonate esters, epoxide, chlorohydrins as well as terminal olefins conjugated with a carbonyl group including ketone, amide, or ester.

The invention is described in greater detail by the following non-limiting examples. Without further elaboration, it is believed that one skilled in the art can, based on the description herein, utilize the present invention to its fullest extent. All publications cited herein are incorporated by reference in their entirety.

Example 1

A microcapsule composition of this invention (i.e., Composition 1), was prepared following the procedure below.
Preparation of a Cationic Microcapsule A cationic microcapsule (Microcapsule 1) was prepared as a first microcapsule following the procedure below using polystyrene sulfonate and CMC as the capsule formation aid. Ninety-six grains of a fragrance accord (International Flavors and Fragrance, Union Beach, N.J.) was weighed out and combined with 24 g of NEOBEE oil M-5 (caprylic/capric triglyceride, Stepan, Chicago, Ill.) and 9.6 g of isocyanate monomer, TAKENATE D110-N (trimethylol propane-adduct of xylylene diisocyanate, Mitsui Chemicals Corporation, Rye Brook, N.Y.), to form the oil phase. In a separate beaker, a solution (130 g) containing 1.0% of FLEXAN II (polystyrene sulfonate, Akzo Nobel, Bridgewater, N.J.) was mixed with a solution (30 g) of 1% CMC (carboxymethyl cellulose, WALOCEL CRT 50000 PA 07, Dow, Midland, Mich.) in water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules. The fragrance emulsion was heated to 35° C. in a round bottom vessel and 10.4 g of 49% branched polyethylenimine (Sigma-Aldrich, St. Louis, Mo.) was added under constant mixing with an overhead mixer. Formation of capsules was immediately visible by optical microscopy. The mixer speed was reduced after the addition of branched polyethylenimine was complete. The capsule slurry was cured at 55° C. for two hours to obtain Microcapsule 1.

Microcapsule 1 thus prepared had a zeta potential of 51.5 mV.

Preparation of an Anionic Microcapsule

An anionic microcapsule (Microcapsule 2) was prepared as a second microcapsule following the procedure below. This second microcapsule contains a microcapsule wall formed of a reaction product of hexamethylene diamine and a polyisocyanate using a mixture of naphthalene sulfonate condensate salt and polyvinylpyrrolidone as the capsule formation aid.

Ninety six grams of a fragrance accord (International Flavors and Fragrance, Union Beach, N.J.) was weighed out and combined with 24 g of Neobee oil (commercially available from Stepan, Chicago, Ill., USA) and 9.6 g of isocyanate monomer, Lupranate® M20 (BASF corporation, Wyandotte, Mich., USA) to form the oil phase. In a separate beaker, a solution (160 g) containing 1% Morwet D-425 (a sodium salt of naphthalene sulfonate condensate, commercially available from Akzo Nobel, Fort Worth, Tex., USA) and 1% polyvinylpyrrolidone aqueous solution (Luviskol® K90, commercially available from BASF, Ludwigshafen, Germany) was used as the aqueous phase. The oil phase was then emulsified into the aqueous phase to form the fragrance emulsion under shearing (Ultra Turrax®, T25 Basic, IIA® WERKE) at 9500 rpm for two minutes.

The fragrance emulsion was then placed in a round bottom vessel and to which 10.8 g of 40% hexamethylene diamine aqueous solution (HMDA) (commercially available from INVISTA, Wichita, Kans., USA) was added under constant mixing with an overhead mixer. Formation of capsule was immediately visible by optical microscopy. The mixer speed was reduced after the addition of HMDA was complete. The capsule slurry was cured at 55° C. for two hours to obtain Microcapsule 2.

Microcapsule 2 thus prepared had a zeta potential of −26 mV.

Preparation of Composition 1

Microcapsule 1 (30 g) was mixed with Microcapsule 2 (30 g) at room temperature for 1 hour to obtain a microcapsule composition of this invention, i.e., Composition 1.

Example 2: Performance of Composition 1 in a Hair Conditioner Base

To evaluate the performance of Composition 1, it was blended with a model hair conditioner base at a level of 1% by weight of the hair conditioner base. The fragrance load was 0.3% neat equivalent.

The perfumery benefit of Composition 1 was evaluated by conducting a personal wash experiment using the standard protocol below. Four hair swatches were washed per sample. For each hair swatch, 1 g an unfragranced shampoo was applied on swatch. The shampoo is lathered into hair by rubbing swatches together clockwise & counterclockwise 10 times each. After the shampoo was set on the swatch for 15 seconds, the swatch was washed in a water flow (37° C., 1 gallon/min) for 45 seconds. Subsequently, the swatch was washed with the hair conditioner containing Composition 1 using the same protocol as the shampoo. After washing, the swatch was hang-dried for 16 hours before being evaluated by a panel of 12 judges. Before and after brushing the swatch, the fragrance intensity was rated from a scale ranging from 0 to 10. A numerical value of 2 would suggest the hair only produce weak intensity while a value of 10 a very strong smell.

Microcapsules 1 and 2 were used as comparative samples following the same blending and hair washing as Composition 1.

The results showed that Composition 1 had a pre-brush fragrance intensity of 3 before the hair swatch was brushed and a post-brush fragrance intensity of 5.8 after the hair swatch was brushed.

By contrast, Microcapsule 1 had a pre-brush fragrance intensity of 2.3 and a post-brush fragrance intensity of 5.6; Microcapsule 2 had a pre-brush fragrance intensity of 1.9 and a post-brush fragrance intensity of 3.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to achieve the purpose of encapsulating an active material, one skilled in the art can design and prepare a capsule composition by using different microcapsules, polyfunctional nucleophiles and/or electrophiles, suitable encapsulating polymers, and/or capsule formation aids, varying the concentrations of these wall-forming materials and/or catalysts to achieve desirable organoleptic or release profiles in a consumable product. Further, the ratios among microcapsules, encapsulating polymers, capsule forming aids, adjuvants, core modifiers, active materials, and catalysts can also be determined by a skilled artisan through assays known in the art to prepare capsule compositions with desirable properties.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A microcapsule composition comprising a first microcapsule and a second microcapsule, wherein
   the first microcapsule has a zeta potential of 10 mV or greater,
   the second microcapsule has a zeta potential of 5 mV or less,
   the weight ratio of the first microcapsule and the second microcapsule is between 1:10 and 10:1,
   the first microcapsule has a first oil core and a first microcapsule wall encapsulating the first oil core,
   the first oil core contains a first active material at a level of 5% to 95% by weight of the first microcapsule,
   the second microcapsule contains a second oil core and a second microcapsule wall encapsulating the second oil core, and
   the second oil core contains a second active material at a level of 5% to 95% by weight of the second microcapsule; and
   wherein the second microcapsule wall is formed from an encapsulating polymer that is not starch.

2. The microcapsule composition of claim 1, wherein the first microcapsule has a zeta potential of 25 mV or greater.

3. The microcapsule composition of claim 1, wherein the first microcapsule has a zeta potential of 40 mV or greater.

4. The microcapsule composition of claim 1, wherein the second microcapsule has a zeta potential of 5 mV to −5 mV.

5. The microcapsule composition of claim 1, wherein the second microcapsule has a zeta potential of −10 mV or less.

6. The microcapsule composition of claim 1, wherein the second microcapsule has a zeta potential of −20 mV or less.

7. The microcapsule composition of claim 2, wherein the second microcapsule has a zeta potential of 5 mV to −5 mV.

8. The microcapsule composition of claim 2, wherein the second microcapsule has a zeta potential of −10 mV or less.

9. The microcapsule composition of claim 2, wherein the second microcapsule has a zeta potential of −20 mV or less.

10. The microcapsule composition of claim 3, wherein the second microcapsule has a zeta potential of 5 mV to −5 mV.

11. The microcapsule composition of claim 3, wherein the second microcapsule has a zeta potential of −10 mV or less.

12. The microcapsule composition of claim 3, wherein the second microcapsule has a zeta potential of −20 mV or less.

13. The microcapsule composition of claim 1, herein each of the first and second active materials, independently, is a fragrance, pro-fragrance, flavor, vitamin or derivative thereof, malodor counteractive agent, anti-inflammatory agent, fungicide, anesthetic, analgesic, antimicrobial active, anti-viral agent, anti-infectious agent, anti-acne agent, skin lightening agent, insect repellant, emollient, skin moisturizing agent, wrinkle control agent, UV protection agent, fabric softener active, hard surface cleaning active, skin or hair conditioning agent, insect repellant, animal repellent, vermin repellent, flame retardant, antistatic agent, nanometer to micron size inorganic solid, polymeric or elastomeric particle, or combination thereof.

14. The microcapsule composition of claim 1, further comprising a deposition aid selected from the group consisting of polyquaternium-4, polyquaternium-5, polyquaternium-6, polyquaternium-7, polyquaternium-10, polyquaternium-16, polyquaternium-22, polyquaternium-24, polyquaternium-28, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, and combinations thereof.

15. The microcapsule composition of claim 1, further comprising a capsule formation aid selected from the group consisting of a polyvinyl alcohol, polystyrene sulfonate, carboxymethyl cellulose, naphthalene sulfonate condensate salt, polyvinylpyrrolidone, copolymer of vinyl pyrrolidone and quaternized dimethylaminoethyl methacrylate, and combination thereof.

16. The microcapsule composition of claim 1, further comprising a third, fourth, fifth, or sixth delivery system.

17. The microcapsule composition of claim 1, wherein the microcapsule composition is in the form of a solid or liquid.

18. A consumer product comprising the microcapsule composition of claim 1.

19. The consumer product of claim 18, wherein the consumer product is a hair care product, a personal care product, a fabric care product, or a home care product.

20. The consumer product of claim 18, wherein the consumer product is a shampoo, hair conditioner, personal wash, shower gel, bar soap, dish detergent, all-purpose cleaner, liquid detergent, powder detergent, scent booster, fabric conditioner, dryer sheet, or fabric refresher.

* * * * *